(12) United States Patent
Poirot et al.

(10) Patent No.: US 12,167,995 B2
(45) Date of Patent: Dec. 17, 2024

(54) [((1R,2S,5R)-2-ISOPROPYL-5-METHYL-CYCLOHEXANECARBONYL)-AMINO]-ACETIC ACID ISOPROPYL ESTER FOR TREATMENT OF CHRONIC COUGH

(71) Applicant: AXALBION SA, Lausanne (CH)

(72) Inventors: Olivier Poirot, Lausanne (CH); Ashley Woodcock, Lausanne (CH)

(73) Assignee: Axalbion SA, Lausanne (CH)

( * ) Notice: Subject to any disclaimer, the term of this patent is extended or adjusted under 35 U.S.C. 154(b) by 0 days.

(21) Appl. No.: 17/618,394

(22) PCT Filed: Jun. 10, 2020

(86) PCT No.: PCT/EP2020/066065
§ 371 (c)(1),
(2) Date: Dec. 10, 2021

(87) PCT Pub. No.: WO2020/249607
PCT Pub. Date: Dec. 17, 2020

(65) Prior Publication Data
US 2022/0265594 A1    Aug. 25, 2022

(30) Foreign Application Priority Data
Jun. 10, 2019 (GB) ..................... 1908219

(51) Int. Cl.
*A61K 31/223* (2006.01)
*A61P 11/14* (2006.01)

(52) U.S. Cl.
CPC ............ *A61K 31/223* (2013.01); *A61P 11/14* (2018.01)

(58) Field of Classification Search
CPC .............................. A61P 11/14; A61K 31/223
See application file for complete search history.

(56) References Cited

U.S. PATENT DOCUMENTS

2012/0251461 A1* 10/2012 Wei .................. A61P 11/06
514/541
2015/0111852 A1* 4/2015 Wei .................. A61P 43/00
514/75

FOREIGN PATENT DOCUMENTS

| JP | 20140503513 A | 2/2014 |
| WO | 2012076831 A1 | 6/2012 |
| WO | 2019/023147 A1 | 1/2019 |
| WO | 2019/219674 A1 | 11/2019 |

OTHER PUBLICATIONS

Millqvist et. al. (Respiratory Medicine (2013) 107:433-438). (Year: 2013).*
Johnson et. al. (Journal of Agricultural and Food Chemistry (2018) 66:2319-2323) (Year: 2018).*
Palombini et. al., (Chest (1999) 116:279-284). (Year: 1999).*
Dicpinigaitis, (Chest (2006) 129: 75S-79S). (Year: 2006).*
Madison et. al., (Expert Opinion on Pharmacotherapy (2003) 4:1039-1048). (Year: 2003).*
Millqvist, (Temperature (2015) 2:172-177). (Year: 2015).*
International Search Report and Written Opinion mailed Aug. 27, 2020 for corresponding International Application No. PCT/EP2020/066065.
Written Opinion of the International Preliminary Examining Authority mailed May 14, 2021 for corresponding International Application No. PCT/EP2020/066065.
Anonymous: "A pilot study of the efficacy, safety, and tolerability of AX-8 for the treatment of refractory chronic cough", Eu Clinical Trials Register, Aug. 31, 2017, XP055710974, URL: https://www.clinicaltrialsregister.eu/ctr-search/trial/2017-003108-27/GB#summary.
Millqvist, E., et al. (2013). "Inhalation of menthol reduces capsaicin cough sensitivity and influences inspiratory flows in chronic cough." Respiratory Medicine, vol. 107, No. 3, pp. 433-438. doi:10.1016/j.rmed.2012.11.017.
Berkhof, F., et al. (2013). "Azithromycin and cough-specific health status in patients with chronic obstructive pulmonary disease and chronic cough: a randomised controlled trial." Respiratory Research, vol. 14, No. 1, p. 125. doi:10.1186/1465-9921-14-125.
National Center for Biotechnology Information. "PubChem Substance Record for SID 376228950, 7SUP5O6AA1, Source: ChemIDplus" PubChem, https://pubchem.ncbi.nlm.nih.gov/substance/376228950. Accessed Dec. 10, 2021.
Search Report dated May 11, 2019 issued in Application No. 1908219.7.
Second Written Opinion Chapter II dated May 14, 2021 issued in Application No. PCT/EP2020/066065.
International Preliminary Report on Patentability dated Sep. 16, 2021 issued in Application No. PCT/EP2020/066065.
Abdulqawi R, Dockry R, Holt K, Layton G, McCarthy BG, Ford AP, Smith JA. P2X3 receptor antagonist (AF-219) in refractory chronic cough: a randomised, double-blind, placebo-controlled phase 2 study. Lancet. Mar. 28, 2015;385 (9974):1198-205. doi: 10.1016/S0140-6736(14)61255-1. Epub Nov. 25, 2014. PMID: 25467586.
Baylie RL, Cheng H, Langton PD, James AF. Inhibition of the cardiac L-type calcium channel current by the TRPM8 agonist, (-)-menthol. J Physiol Pharmacol. Oct. 2010;61(5):543-50. PMID: 21081797.
Belvisi MG, Birrell MA, Wortley MA, Maher SA, Satia I, Badri H, Holt K, Round P, McGarvey L, Ford J, Smith Ja. XEN-D0501, a Novel Transient Receptor Potential Vanilloid 1 Antagonist, Does Not Reduce Cough in Patients with Refractory Cough. Am J Respir Crit Care Med. Nov. 15, 2017;196(10):1255-1263. doi: 10.1164/rccm.201704-0769OC. PMID: 28650204.

(Continued)

*Primary Examiner* — Marcos L Sznaidman
(74) *Attorney, Agent, or Firm* — Venable LLP

(57) ABSTRACT

The present invention pertains generally to the field of therapy. More specifically the present invention pertains to a certain compound, [((1R,2S,5R)-2-isopropyl-5-methyl-cyclohexanecarbonyl)-amino]-acetic acid isopropyl ester (also referred to herein as "AX-8" or "Gly-O-iPr"), as described herein, for use in a method of treatment of the human or animal body by therapy, more specifically, for use in a method of treatment of chronic cough (CC), including, for example, refractory chronic cough (RCC) and idiopathic chronic cough (ICC), as described herein.

47 Claims, 9 Drawing Sheets

(56) References Cited

OTHER PUBLICATIONS

Birrell et al., 2009, "TRPA1 Agonists Evoke Coughing in Guinea Pig and Human Volunteers", Am J Respir Crit Care Med., vol. 180, pp. 1042-1047.
Birring et al., 2003, "Development of a symptom specific health status measure for patients with chronic cough: Leicester Cough Questionnaire (LCQ)", Thorax, vol. 58, pp. 339-343.
Birring SS. The search for the hypersensitivity in chronic cough. Eur Respir J. Feb. 8, 2017;49(2):1700082. doi: 10.1183/13993003. 00082-2017. PMID: 28179446.
Brozmanova M, Mazurova L, Ru F, Tatar M, Kollarik M. Comparison of TRPA1-versus TRPV1-mediated cough in guinea pigs. Eur J Pharmacol. Aug. 15, 2012;689(1-3):211-8. doi: 10.1016/j.ejphar.2012.05.048. Epub Jun. 7, 2012. PMID: 22683866; Pmcid: PMC4667741.
Canning BJ, Chang AB, Bolser DC, Smith JA, Mazzone SB, McGarvey L; Chest Expert Cough Panel. Anatomy and neurophysiology of cough: Chest Guideline and Expert Panel report. Chest. Dec. 2014;146(6):1633-1648. doi:10.1378/chest.14-1481. PMID:25188530; PMCID: PMC4251621.
Chow, Lillian, et al. "Animal Models of Chronic Obstructive Pulmonary." COPD: An Update in Pathogenesis and Clinical Management (2018): 1.
Chung, Kian Fan, Lorcan McGarvey, and Stuart B. Mazzone. "Chronic cough as a neuropathic disorder." The lancet Respiratory medicine 1.5 (2013): 414-422.
Chung KF. Approach to chronic cough: the neuropathic basis for cough hypersensitivity syndrome. J Thorac Dis. Oct. 2014;6(Suppl 7):S699-707. doi: 10.3978/j.issn.2072-1439.2014.08.41. PMID: 25383203; PMCID: PMC4222934.
Dong, Peijian, et al. "A TRPM8 agonist AX-8 inhibits capsaicin-induced cough in guinea pig." Chest 149.4 (2016): A545.
Ford, Alexander C., et al. "Cough in the community: a cross sectional survey and the relationship to gastrointestinal symptoms." Thorax 61.11 (2006): 975-979.
Galeotti, Nicoletta, et al. "Menthol: a natural analgesic compound." Neuroscience letters 322.3 (2002): 145-148.
Gavliakova, Silvia, et al. "Analysis of pathomechanisms involved in side effects of menthol treatment in respiratory diseases." (2013).
Gibson PG, Vertigan AE. Management of chronic refractory cough. BMJ. Dec. 14, 2015;351:h5590. doi: 10.1136/bmj.h5590. PMID: 26666537.
Haidl et al., 2001, "Does the inhalation of a 1% L-menthol solution in the premedication of fiberoptic bronchoscopy affect coughing and the sensation of dyspnea?", Pneumol. Stuttg. Ger., vol. 55, pp. 115-119.
Khalid S, Murdoch R, Newlands A, Smart K, Kelsall A, Holt K, Dockry R, Woodcock A, Smith JA. Transient receptor potential vanilloid 1 (TRPV1) antagonism in patients with refractory chronic cough: a double-blind randomized controlled trial. J Allergy Clin Immunol. Jul. 2014;134(1):56-62. doi: 10.1016/j.jaci.2014.01.038. Epub Mar. 22, 20142. PMID: 24666696.
Karashima Y, Damann N, Prenen J, Talavera K, Segal A, Voets T, Nilius B. Bimodal action of menthol on the transient receptor potential channel TRPA1. J Neurosci. Sep. 12, 2007;27(37):9874-84. doi: 10.1523/JNEUROSCI.2221-07.2007. PMID: 17855602; PMCID: PMC6672629.
Kenia P, Houghton T, Beardsmore C. Does inhaling menthol affect nasal patency or cough? Pediatr Pulmonol. Jun. 2008;43(6):532-7. doi: 10.1002/ppul.20797. PMID: 18435479.
Maher, S. A., et al. "P6 Menthol has beneficial effects in the airways through a Trpm8-independent mechanism." (2014): A79-A80.
Mazzone, Stuart B., Kian Fan Chung, and Lorcan McGarvey. "The heterogeneity of chronic cough: a case for endotypes of cough hypersensitivity." The Lancet Respiratory medicine 6.8 (2018): 636-646.
McGarvey LP. Idiopathic chronic cough: a real disease or a failure of diagnosis? Cough. Sep. 23, 2005;1:9. doi: 10.1186/1745-9974-1-9. PMID: 16270939; PMCID: PMC1277011.

Morice, A. H., Lorcan McGarvey, and I. Pavord. "Recommendations for the management of cough in adults." Thorax 61.suppl 1 (2006): i1-i24.
Morice AH, Faruqi S, Wright CE, Thompson R, Bland JM. Cough hypersensitivity syndrome: a distinct clinical entity. Lung. Feb. 2011; 189(1):73-9. doi: 10.1007/s00408-010-9272-1. Epub Dec. 14, 2010. PMID: 21240613.
Morice, Alyn Hugh, et al. "The Effect of MK-7264, a P2X3 antagonist, on cough reflex sensitivity in a randomized crossover trial of healthy and chronic cough subjects. " (2017).
Oz M, El Nebrisi EG, Yang KS, Howarth FC, Al Kury LT. Cellular and Molecular Targets of Menthol Actions. Front Pharmacol. Jul. 18, 2017;8:472. doi: 10.3389/fphar.2017.00472. PMID: 28769802; PMCID: PMC5513973.
Pavord ID, Chung KF. Management of chronic cough. Lancet. Apr. 19, 2008;371(9621):1375-84. doi: 10.1016/S0140-6736(08)60596-6. PMID: 18424326.
Polverino M, Polverino F, Fasolino M, Ando F, Alfieri A, De Blasio F. Anatomy and neuro-pathophysiology of the cough reflex arc. Multidiscip Respir Med. Jun. 18, 2012;7(1):5. doi: 10.1186/2049-6958-7-5. PMID: 22958367; PMCID: PMC3415124.
Ryan NM, Vertigan AE, Birring SS. An update and systematic review on drug therapies for the treatment of refractory chronic cough. Expert Opin Pharmacother. May 2018; 19(7):687-711. doi: 10.1080/14656566.2018.1462795. Epub Apr. 16, 2018. PMID: 29658795; PMCID: PMC5935050.
Smith, J. A., et al. "S27 The effect of P2X3 antagonism (AF-219) on experimentally evoked cough in healthy volunteers and chronic cough patients." (2016): A17-A17.
Smith, Jaclyn, et al. "Inhibition of P2X3 by MK-7264 reduces 24-hour cough frequency in a randomized, controlled, Phase 2b clinical trial." (2017).
Smith, Jaclyn A., et al. "MK-7264, a P2X3 receptor antagonist, reduces cough frequency in patients with refractory chronic cough: results from a randomized, controlled, phase 2b clinical trial." B14. Clinical Trials Across Pulmonary Disease. American Thoracic Society, 2017. A7608-A7608.
Smith, Jaclyn A., et al. "Effects of a novel sodium channel blocker, GSK2339345, in patients with refractory chronic cough." International journal of clinical pharmacology and therapeutics 55.9 (2017): 712.
Song WJ, Morice AH. Cough Hypersensitivity Syndrome: A Few More Steps Forward. Allergy Asthma Immunol Res. Sep. 2017;9(5):394-402. doi: 10.4168/aair.2017.9.5.394. PMID: 28677352; PMCID: PMC5500693.
Takaishi M, Uchida K, Suzuki Y, Matsui H, Shimada T, Fujita F, Tominaga M. Reciprocal effects of capsaicin and menthol on thermosensation through regulated activities of TRPV1 and TRPM8. J Physiol Sci. Mar. 2016;66(2):143-55. doi: 10.1007/s12576-015-0427-y. Epub Dec. 8, 2015. PMID: 26645885; PMCID: PMC4752590.
Vogt-Eisele AK, Weber K, Sherkheli MA, Vielhaber G, Panten J, Gisselmann G, Hatt H. Monoterpenoid agonists of TRPV3. Br J Pharmacol. Jun. 2007; 151(4):530-40. doi: 10.1038/sj.bjp.0707245. Epub Apr. 10, 2007. PMID: 17420775; PMCID: PMC2013969.
Xu, Xianghuai, et al. "Establishment of Chronic Cough Model in Guinea Pigs by Citric Acid Inhalation." Chest 149.4 (2016): A543.
Bonvini, Sara J., et al. "Transient receptor potential cation channel, subfamily V, member 4 and airway sensory afferent activation: role of adenosine triphosphate." Journal of Allergy and Clinical Immunology 138.1 (2016): 249-261.
EudraCT No. 2013-002728-17, "A Phase 2a, Multi-Centre, Randomised, Double-Blind, Parallel Group, Placebo-Controlled Study to Evaluate Efficacy, Safety and Tolerability of Inhaled GRC 17536, Administered for 4 weeks, in Patients with Refractory Chronic Cough", https://www.clinicaltrialregister.eu/ctr-search/trial/2013-002728-17/GB.
Ludbrook, V. J., et al. "S27 A placebo-controlled, double-blind, randomised, crossover study to assess the efficacy, safety and tolerability of TRPV4 inhibitor GSK2798745 in participants with chronic cough." Thorax 74.Suppl 2 (2019):A18.
Mukhopadhyay, Indranil, Abhay Kulkarni, and Neelima Khairatkar-Joshi. "Blocking TRPA1 in respiratory disorders: does it hold a promise?. " Pharmaceuticals 9.4 (2016): 70.

(56) References Cited

OTHER PUBLICATIONS

Smith JA, Kitt MM, Morice AH, Birring SS, McGarvey LP, Sher MR, Li YP, Wu WC, Xu ZJ, Muccino DR, Ford AP; Protocol 012 Investigators. Gefapixant, a P2X3 receptor antagonist, for the treatment of refractory or unexplained chronic cough: a randomised, double-blind, controlled, parallel-group, phase 2b trial. Lancet Respir Med. Aug. 2020;8 (8):775-785. doi: 10.1016/S2213-2600(19)30471-0. Epub Feb. 25, 2020. PMID: 32109425.
Berkhof, Farida F., et al. "Azithromycin and cough-specific health status in patients with chronic obstructive pulmonary disease and chronic cough: a randomised controlled trial." Respiratory research 14.1 (2013): 1-8.
National Center for Biotechnology Information. "PubChem Substance Record for SID 2018, SID 2018, Source: BioCyc" PubChem, https://pubchem.ncbi.nlm.nih.gov/substance/2018. Accessed Nov. 21, 2022.
EU Clinical Trial for EudraCT No. 2017-003108-27, Publication Date Jun. 27, 2019.
EU Clinical Trial for EudraCT No. 2016-004803-30, Publication Date Jun. 12, 2022.
Melanaphy D, Johnson CD, Kustov MV, Watson CA, Borysova L, Burdyga TV, Zholos AV . Ion channel mechanisms of rat tail artery contraction-relaxation by menthol involving, respectively, TRPM8 activation and L-type Ca2+ channel Inhibition. Am J Physiol Heart Circ Physiol. Dec. 1, 2016;311(6):H1416-H1430. doi: 10.1152/ajpheart.00222.2015. Epub Oct. 7, 2016. PMID: 27765744; Pmcid: PMC5206336.
Bolser DC. Experimental models and mechanisms of enhanced coughing. Pulm Pharmacol Ther. 2004;17(6):383-8. doi: 10.1016/j.pupt.2004.09.016. PMID: 15564080; PMCID: PMC3121141.
Millqvist E, Ternesten-Hasséus E, Bende M. Inhalation of menthol reduces capsaicin cough sensitivity and influences Inspiratory flows in chronic cough. Respir Med. Mar. 2013; 107(3):433-8. doi: 10.1016/j.rmed.2012.11.017. Epub Dec. 23, 2012. PMID: 23266255.
Eugenio Cavalli et al., "The Neuropathic Pain: An Overview of the Current Treatment and Future Therapeutic Approaches," 33 Int. J. Immunopathol. Pharmacol. 1-10 (Mar. 2019).
Peter G. Gibson et al., "Management of Chronic Refractory Cough," BMJ 351, h5590: 1-12 (2015).
Notice of Reasons for Rejections in Japanese Application No. 2021-571758 (Jun. 2022).
Office Action in Eurasian Application No. 202193006 (May 2022).
Office Action in Eurasian Application No. 202193006 (Dec. 2022).
Office Action in Eurasian Application No. 202193006 (Jul. 2023).
First Objective Examination Report in Saudi Arabian Application No. 521431061 (Nov. 2022).

\* cited by examiner

[((1R,2S,5R)-2-ISOPROPYL-5-METHYL-CYCLOHEXANECARBONYL)-AMINO]-ACETIC ACID ISOPROPYL ESTER FOR TREATMENT OF CHRONIC COUGH

RELATED APPLICATIONS

The present application is a U.S. National Stage application under 35 USC 371 of PCT Application Serial No. PCT/EP2020/066065, filed on 10 Jun. 2020; which claims priority from GB Patent Application No. 1908219.7, filed 10 Jun. 2019, the entirety of both of which are incorporated herein by reference.

TECHNICAL FIELD

The present invention pertains generally to the field of therapy. More specifically the present invention pertains to a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, for use in a method of treatment of the human or animal body by therapy, more specifically, for use in a method of treatment of chronic cough (CC), including, for example, refractory chronic cough (RCC) and idiopathic chronic cough (ICC), as described herein.

BACKGROUND

A number of publications are cited herein in order to more fully describe and disclose the invention and the state of the art to which the invention pertains. Each of these publications is incorporated herein by reference in its entirety into the present disclosure, to the same extent as if each individual publication was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Cough

A cough is a sudden and often repetitively occurring, protective reflex, which helps to clear the large breathing passages from fluids, irritants, foreign particles, and microbes. The cough reflex consists of three phases: an inhalation; a forced exhalation against a closed glottis; and a violent release of air from the lungs following opening of the glottis, usually accompanied by a distinctive sound.

Cough is a non-specific reaction to irritation anywhere from the pharynx to the lungs. The cough reflex is triggered by mechanical or inflammatory changes or irritants in the airways.

The Cough Reflex

Cough occurs through the stimulation of a complex reflex arc (see, e.g., Polverino et al., 2012; Canning et al., 2014) constituted by:

Sensory termini expressing cough receptors: termini of sensory afferent fibres innervating extra-thoracic locations (e.g., nose, oropharynx, larynx, upper trachea), intra-thoracic locations (e.g., lower trachea and large central bronchi), or other locations (e.g., tympanic membrane, diaphragm, oesophagus, stomach).

Afferent pathway sensory nerve fibres, mainly vagal (cranial nerve X) as well as trigeminal (cranial nerve V) and glossopharyngeal (cranial nerve IX).

Central pathway (cough centre): a central coordinating/convergence region for coughing located in the brainstem (the core of the cough network is located in the ventrolateral region of the medulla).

Efferent pathway impulses from the cough centre travel via the vagus, phrenic, and spinal motor nerves to the diaphragm, abdominal wall, and muscles.

Prevalence of Cough

Cough is one of the most common reasons for adults and children to visit their general practitioner. For example, at any one time, 20% of the United Kingdom (UK) population have a troublesome cough and sufferers consume 75 million doses of over-the-counter (OTC) antitussive medication annually (see, e.g., Birring et al., 2003). One study to grade cough severity found 7% of a general population had cough sufficient to interfere with activities of daily living on at least a weekly basis in the UK (see, e.g., Ford et al., 2006).

Classification of Cough

Cough can be divided into: (a) acute self-limiting cough, lasting less than three weeks; (b) subacute cough, lasting for an intermediate period of 3-8 weeks; and (c) chronic cough (CC), which lasts for a longer period (typically, more than 8 weeks in adults and more than 4 weeks in children).

Acute cough can also be classified according to its cause: infectious (caused by an infection) or non-infectious. Infectious causes of acute cough include: viral upper respiratory infections (the common cold); COVID-19 disease; sinus infections; acute bronchitis; pneumonia; and whooping cough. Non-infectious causes of acute cough include: exposure to chemicals, exposure to irritants; and environmental allergies.

Chronic cough (CC) is common in clinical practice and is associated with decreased quality of life. It can persist for many months, and sometimes years, and is a troublesome and difficult-to-treat symptom.

Chronic Cough (CC) as a Neuropathic Disorder

There is a widespread clinical recognition that CC reflects a neuropathic state whereby the basal protective cough reflex has been transformed to a level of heightened sensitivity such that cough is triggered by low-level stimuli not normally sufficient to cause cough (e.g., a change in ambient temperature, taking a deep breath, laughing, talking on the telephone, exposure to odours or aerosols, etc.; a concept termed allotussia) and by smaller amounts of known cough-inducing stimuli (e.g., capsaicin, citric acid, etc.; a concept termed hypertussia) (see, e.g., Chung et al., 2013; Mazzone et al., 2018; Gibson et al, 2015). In most CC patients, this hypersensitivity is also associated with abnormal sensations such persistent urge-to-cough and throat irritation, throat tickle, or throat itch (see, e.g., Song et al., 2017; Gibson et al, 2015). Both the motor (spontaneous cough) and sensory consequences of this hypersensitivity are distressful for CC patients and should be addressed by treatment.

This concept is often referred as the cough hypersensitivity syndrome (CHS) or cough reflex hypersensitivity (CRH) (see, e.g., Chung, 2014; Birring, 2017; Song et al., 2017; Morice et al., 2011; Ryan et al., 2018; Mazzone et al., 2018). The conventional view is that an inflammation-induced disorder or injury of the nervous system (neuroinflammation) leads to CHS whereby neural pathways (in the airways and in the brain) have become affected by a heterogeneous range of factors including infection and physical and chemical irritants (see, e.g., Mazzone et al., 2018; Chung et al., 2013).

By analogy with neuropathic pain (see, e.g., Chung et al., 2013), CHS can be due to: peripheral sensitization; central sensitization (cough centre); and/or cortical and subcortical maladaptive plasticity.

The term sensory neuropathic cough is now often recognized in cough guidelines. It has overlap with laryngeal paraesthesia and laryngeal hypersensitivity syndrome (LHS) and cough hypersensitivity (CHS) syndromes (see, e.g., Gibson et al., 2015; Ryan et al., 2018). The term laryngeal hypersensitivity (LHS) is often used interchangeably with sensory neuropathic cough.

Types of Chronic Cough (CC)

Some patients have explained chronic cough, that is, chronic cough as a symptom of a diagnosed condition. Common causes of chronic cough are, for example, asthma, eosinophilic bronchitis, post-nasal drip syndrome (PNDS), gastro-oesophageal reflux disease (GORD), bronchiectasis chronic obstructive pulmonary disease (COPD), and idiopathic pulmonary fibrosis (IPF).

However, in many cases, despite extensive evaluation and trials of therapy, the chronic cough remains both unexplained and refractory to treatment in chronic coughers (up to 46% of patients seen in secondary care; see, e.g., Pavord et al., 2008; McGarvey, 2005).

Chronic cough that persists despite assessment and treatment according to an accepted guideline is often referred to as refractory chronic cough (RCC) (sometimes also as chronic refractory cough), that is, chronic cough that is refractory to treatment of the associated condition. Chronic cough that has no identified cause is often referred to as unexplained or idiopathic chronic cough (ICC). Refractory chronic cough is sometimes also referred to as idiopathic chronic cough, for example, when the cause of the chronic cough is often no longer the original associated condition, but some other, as yet undetermined condition (e.g., a neurological condition) (see, e.g., Gibson et al., 2015; Ryan et al., 2018).

For example, a patient suffering from chronic cough is diagnosed with asthma and treated for the asthma. Most of the asthma symptoms are improved; however, the chronic cough is not improved. The patient, who was initially considered to have explained chronic cough (due to asthma) is now diagnosed with refractory chronic cough (because it is refractory to the treatment of the associated condition, asthma) or idiopathic chronic cough (because, now, the associated condition causing the persistent chronic cough is unknown, or not yet known).

Because patients with unexplained chronic cough often receive specific therapies, such as inhaled corticosteroids or proton pump inhibitors, they can also be classified as having RCC.

Consequently, the terms refractory chronic cough (RCC), chronic refractory cough, unexplained chronic cough, and idiopathic chronic cough (ICC) are often used interchangeably (and sometimes inconsistently and/or incorrectly) in the literature and in clinical practice.

Treatment of Cough

In most cases, cough is treated by treating the underlying cause. However, in some cases (e.g., when the underlying cause cannot be identified, or cannot be readily or quickly treated), symptomatic treatment of cough is recommended.

Cough suppressants may be useful, particularly if sleep is disturbed. However, they may cause sputum retention, and this may be harmful in patients with chronic bronchitis or bronchiectasis.

There are various drugs which may partially suppress cough, although the cough reflex is exceedingly difficult to abolish. There is a lack of evidence for the efficacy of most antitussive drugs and many of them, especially narcotics, induce adverse side-effects. Moreover, abuse and overdose associated with narcotic cough suppressant is a major public health concern, especially in US. The British Thoracic Society guidelines state: "There are no effective treatments controlling the cough response per se with an acceptable therapeutic ratio" (see, e.g., Morice et al., 2006).

Codeine (a narcotic drug) may be effective but can cause dependence. Dextromethorphan (an opioid derivative, non-narcotic) and pholcodine (also known as homocodeine) have fewer side-effects. Morphine or diamorphine at higher doses may be used for severe, distressing cough in palliative care.

Benzonatate (marketed under the names Tessalong, Tessalon Perles, and Zonatuss) is currently the only non-narcotic prescription drug for cough suppression.

Sedating antihistamines are used as the cough suppressant component of many compound cough preparations on sale to the public.

Mucolytics (e.g., carbocisteine or erdosteine) are prescribed to facilitate expectoration by reducing sputum viscosity. In some patients with COPD and a chronic productive cough, mucolytics can reduce exacerbations. Mucolytic therapy should be stopped if there is no benefit after a four-week trial. Steam inhalation with postural drainage is effective in bronchiectasis and in some cases of chronic bronchitis.

Demulcent cough preparations contain soothing substances such as syrup or glycerol and may be used to relieve a dry irritating cough. Preparations such as simple linctus have the advantage of being harmless and inexpensive.

Expectorants are claimed to promote expulsion of bronchial secretions but there is no evidence that any drug can specifically facilitate expectoration.

Treatment of Chronic Cough

At present, there is no dedicated treatment for chronic cough (CC), whether as a symptom of a diagnosed condition or a condition itself.

Among CC patients, those with RCC are the ones with the highest need. Only a few treatment options exist for patients with RCC (see, e.g., Gibson et al., 2015; Ryan et al., 2018). For that reason, pharmaceutical companies currently focus on RCC patients. Moreover, patients with RCC provide a useful model for studying antitussive agents for CC as cough frequency is high and stable over time making such clinical studies powerful for demonstrating treatment effects.

Centrally acting neuromodulators such as morphine (an opioid), amitriptyline (a tricyclic antidepressant and inhibitor of serotonin reuptake), gabapentin and pregabalin (two blockers of some voltage-gated calcium channels expressed in the central nervous 35 system) may be useful for treatment of RCC (see, e.g., Gibson et al., 2015; Ryan et al., 2018).

Speech therapy techniques have also shown benefit for treatment of RCC (see, e.g., Gibson et al., 2015; Ryan et al., 2018).

Patients and clinicians frequently try over-the-counter (OTC) medications available for acute cough (such as dextromethorphan, codeine, and menthol), but with little benefit.

Treatments recently or currently under development for RCC have new biological targets, which were not previously targeted for acute cough, such as α7-nACh, P2X3, NK1, TRPV1, TRPV4, and TRPA1 receptors (see, e.g., Ryan et al., 2018; Abdulqawi et al., 2015; Belvisi et al., 2017; Khalid et al., 2014; Smith et al., 2017a; Smith et al., 2017b; Smith et al., 2020; EudraCT Number 2013-002728-17).

Empirically, treatments for acute cough often have no effect for RCC, and vice versa.

Even if a treatment is known to be effective for acute cough, it cannot be predicted (with reasonably certainty) that it would also be effective for treating chronic cough. For example, two TRPV1 antagonists (XEN-D0501 and SB-705498) inhibit acute cough induced by capsaicin (see, e.g., Belvisi et al., 2017; Khalid et al., 2014), but do not reduce cough frequency in RCC patients. Conversely, MK-7264 (also known as AF-219 and Gefapixant), a P2X3 antagonist, is efficient in decreasing cough frequency in RCC patients but is not effective for acute cough induced by the tussive stimulus capsaicin (an irritant and agonist of TRPV1) in RCC patients or in healthy subjects (see, e.g., Abdulqawi et al., 2015; Smith et al., 2016; Morice et al., 2017).

In the present context, non-clinical studies have demonstrated that AX-8 inhibits cough induced by an irritant (i.e., capsaicin, a TRPV1 agonist). However, based on the current state of the art, the skilled person could not have predicted (with reasonably certainty) that AX-8 would also be effective for treating chronic cough (CC), let alone refractory chronic cough (RCC).

Animal Models for Cough

There are no perfect animal models of the human diseases associated with acute or chronic cough. Although existing models approximate these human conditions, the peculiarities of, for example, GORD, asthma, COPD, and various respiratory tract infections, are not reliably reproduced. Since coughing in humans during illness is spontaneous, it would be ideal to study animals that had developed spontaneous cough. But this is essentially never done, with coughing in animals typically studied in response to artificial delivery of a tussive stimulus (see, e.g., Canning et al., 2008).

For COPD, there is only one model in ferret with increased early morning spontaneous cough (but not chronic cough), and all other models do not have spontaneous cough (see, e.g., Chow et al., 2017). Diverse animal models of enhanced cough have been developed, but none reproduce the features of RCC (see, e.g., Bolser, 2004; Xu et al., 2016).

Furthermore, the physiology and pharmacology of spontaneous coughing and induced coughing is likely to be different. Consequently:

The molecular mechanisms that cause and maintain CC are poorly understood, which explains the limited availability of antitussive medications for CC.

Prospective drugs for the treatment of CC cannot be validated by using animal models.

Results from currently available animal models (e.g., cough induced by inhaled capsaicin or citric acid in guinea pig) cannot be translated to efficacy for CC.

Since the predictive value of animal models for cough in chronic cough is so limited, the skilled person cannot predict (with reasonable certainty) that a particular treatment will, in fact, be useful for the treatment of chronic cough, let alone RCC. This situation is illustrated by the failure of proof-of-concept trials for the treatment of RCC, when studies in animal models had positive outcomes (see, e.g., Belvisi et al., 2017; Khalid et al., 2014; Smith et al., 2017c; Smith et al., 2020; Ludbrook et al., 2019; Mukhopadhyay et al., 2016; Bonvini et al., 2016; EudraCT number 2013-002728-17).

Therefore, until the current human clinical trial was completed (and found to be successful), and it had been demonstrated (via the clinical trial data) that AX-8 in fact is useful for the treatment of CC in RCC/ICC patients, that outcome could not have been predicted (with reasonable certainty).

Known Compound AX-8/Gly-O-iPr

The compound, [((1R,2S,5R)-2-isopropyl-5-methyl-cyclohexanecarbonyl)-amino]-acetic acid isopropyl ester (also referred to herein as "AX-8" or "Gly-O-iPr") was described in Wei et al., 2012. See, e.g., page 6 therein.

The use of the compound for the treatment of "cough" is also described therein. See, e.g., claim 53 at page 34 therein.

Study 4 (see page 14 therein) describes the treatment of a patient's dry scratchy throat and cough that was associated with sensitization to cat litter box dust and aggravated by a seasonal allergy to grass pollen.

Study 5 (see pages 14-15 therein) describes treatment of a patient's intense coughing fit that was triggered by eating a piece of fish that was heavily spiced with chili peppers.

Study 6 (page 15 therein) describes treatment of cough in a patient with adult onset asthma aggravated by a seasonal allergy to tree pollen.

Coughing in the aforementioned studies was provoked by irritants and allergens.

Nowhere in Wei et al., 2012 is there any teaching or suggestion of the treatment of chronic cough (CC), let alone refractory chronic cough (RCC) or idiopathic chronic cough (ICC).

SUMMARY OF THE INVENTION

One aspect of the invention pertains to a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, for use in a method of treatment of the human or animal body by therapy, more specifically, for use in a method of treatment of chronic cough (CC), including, for example, refractory chronic cough (RCC) and idiopathic chronic cough (ICC), and as described herein.

Another aspect of the present invention pertains to use a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, in the manufacture of a medicament for treatment, more specifically, for the treatment of chronic cough (CC), including, for example, refractory chronic cough (RCC) and idiopathic chronic cough (ICC), and as described herein.

Another aspect of the present invention pertains to a method of treatment, more specifically, a method of treatment of chronic cough (CC), including, for example, refractory chronic cough (RCC) and idiopathic chronic cough (ICC), and as described herein, comprising administering to a patient in need of treatment a therapeutically effective amount of a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, preferably in the form of a pharmaceutical composition.

Another aspect of the present invention pertains to a kit comprising (a) a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, preferably provided as a pharmaceutical composition and in a suitable container and/or with suitable packaging; and (b) instructions for its use, for example, written instructions on how to administer the compound for the treatment of chronic cough (CC), including, for example, refractory chronic cough (RCC) and idiopathic chronic cough (ICC), and as described herein.

As will be appreciated by one of skill in the art, features and preferred embodiments of one aspect of the invention will also pertain to other aspects of the invention.

DETAILED DESCRIPTION OF THE INVENTION

Compound

Figure 1:
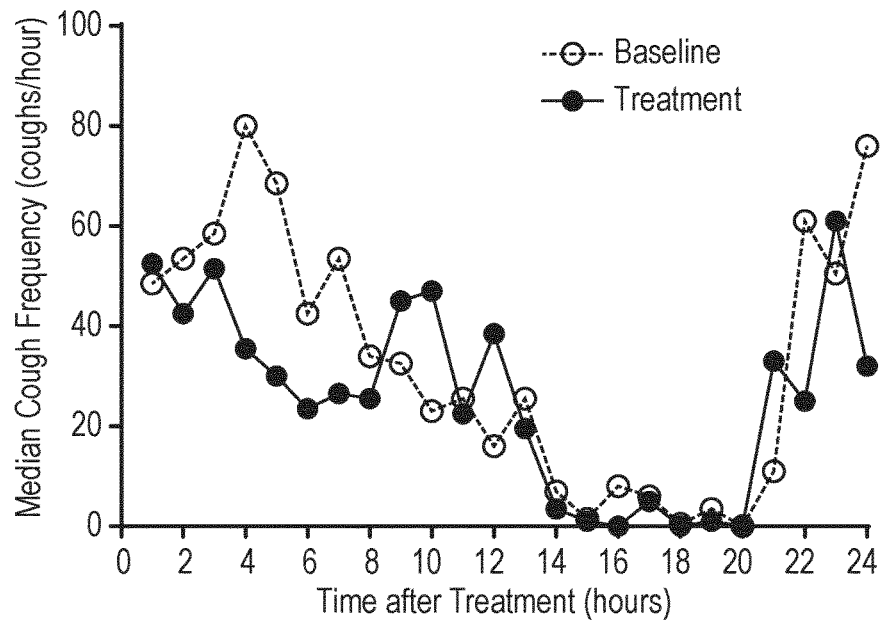
FIG. 1 is a graph of median cough frequency (coughs/hour) versus time after treatment (hours) for baseline (open circles) and treatment (filled circles).

The present invention pertains to a compound that is [((1R,2S,5R)-2-isopropyl-5-methyl-cyclohexanecarbonyl)-amino]-acetic acid isopropyl ester (also referred to herein as "AX-8" or "Gly-O-iPr", shown below), or a pharmaceutically acceptable salt, hydrate, or solvate thereof, as described herein, for use in a method of treatment of the human or animal body by therapy, more specifically, for use in a method of treatment of chronic cough (CC), including, for example, refractory chronic cough (RCC) and idiopathic chronic cough (ICC), and as described herein.

| Code Name | Chemical Name etc. | Chemical Structure |
|---|---|---|
| "AX-8" "Gly-O-iPr" | [((1R,2S,5R)-2-isopropyl-5-methyl-cyclohexanecarbonyl)-amino]-acetic acid isopropyl ester Formula: $C_{16}H_{29}NO_3$ Formula Weight: 283.41 | 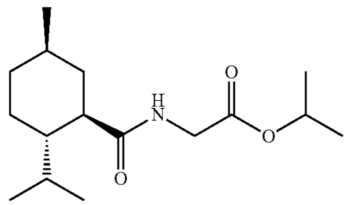 [SMILES: CC(C)OC(=O)CNC(=O)[C@@H]1C[C@H](C)CC[C@H]1C(C)C] |

The compound is structurally related to (−)-menthol, and has the same chiral centres, in the same configuration, as those found in (−)-menthol.

| Name | Chemical Name | Chemical Structure |
|---|---|---|
| (−)-menthol | (1R,2S,5R)-2-isopropyl-5-methyl-cyclohexanol | 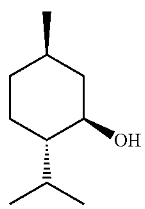 |

In structural terms, the compound may conveniently be described as the isopropyl ester of the glycine amide of the carboxylic acid corresponding to (−)-menthol.

It may also be conveniently described as a p-menthane carboxamide.

In one embodiment, the compound is [((1R,2S,5R)-2-isopropyl-5-methyl-cyclohexanecarbonyl)-amino]-acetic acid isopropyl ester or a pharmaceutically acceptable salt, hydrate, or solvate thereof.

In one embodiment, the compound is [((1R,2S,5R)-2-isopropyl-5-methyl-cyclohexanecarbonyl)-amino]-acetic acid isopropyl ester or a pharmaceutically acceptable salt thereof.

In one embodiment, the compound is [((1R,2S,5R)-2-isopropyl-5-methyl-cyclohexanecarbonyl)-amino]-acetic acid isopropyl ester.

Uses

The compound, [((1R,2S,5R)-2-isopropyl-5-methyl-cyclohexanecarbonyl)-amino]-acetic acid isopropyl ester (also referred to herein as "AX-8" or "Gly-O-iPr"), as described herein, is useful, for example, in the treatment of chronic cough (CC), including, for example, refractory chronic cough (RCC) and idiopathic chronic cough (ICC), and as described herein.

Use in Methods of Therapy

One aspect of the invention pertains to compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, for use in a method of treatment of the human or animal body by therapy, more specifically, for use in a method of treatment of chronic cough (CC), including, for example, refractory chronic cough (RCC) and idiopathic chronic cough (ICC), and as described herein.

One aspect of the invention pertains to a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, in combination with one or more (e.g., 1, 2, 3, 4) additional therapeutic agents, as described herein, for use in a method of treatment of the human or animal body by therapy, more specifically, for use in a method of treatment of chronic cough (CC), including, for example, refractory chronic cough (RCC) and idiopathic chronic cough (ICC), and as described herein.

Use in the Manufacture of Medicaments

One aspect of the present invention pertains to use of a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, in the manufacture of a medicament for treatment, more specifically, for the treatment of chronic cough (CC), including, for example, refractory chronic cough (RCC) and idiopathic chronic cough (ICC), and as described herein.

In one embodiment, the medicament comprises the compound.

One aspect of the present invention pertains to use of a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, and one or more (e.g., 1, 2, 3, 4) additional therapeutic agents, as described herein, in the manufacture of a medicament for treatment, more specifically, for the treatment of chronic cough (CC), including, for example, refractory chronic cough (RCC) and idiopathic chronic cough (ICC), and as described herein.

In one embodiment, the medicament comprises the compound and the one or more (e.g., 1, 2, 3, 4) additional therapeutic agents.

Methods of Treatment

One aspect of the present invention pertains to a method of treatment, more specifically, a method of treatment of chronic cough (CC), including, for example, refractory chronic cough (RCC) and idiopathic chronic cough (ICC), and as described herein, comprising administering to a patient in need of treatment a therapeutically effective amount of a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, preferably in the form of a pharmaceutical composition.

One aspect of the present invention pertains to a method of treatment, more specifically, a method of treatment of chronic cough (CC), including, for example, refractory chronic cough (RCC) and idiopathic chronic cough (ICC), and as described herein, comprising administering to a patient in need of treatment a therapeutically effective amount of a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, preferably in the form of a pharmaceutical composition, and one or more (e.g., 1, 2, 3, 4) additional therapeutic agents, as described herein, preferably in the form of a pharmaceutical composition.

Kits

Another aspect of the present invention pertains to a kit comprising (a) a compound that is [((1R,2S,5R)-2-isopropyl-5-methyl-cyclohexanecarbonyl)-amino]-acetic acid isopropyl ester (also referred to herein as "AX-8" or "Gly-O-iPr"), or a pharmaceutically acceptable salt, hydrate, or solvate thereof, as described herein, preferably provided as a pharmaceutical composition and in a suitable container and/or with suitable packaging; and (b) instructions for its use, for example, written instructions on how to administer the compound for the treatment of chronic cough (CC), including, for example, refractory chronic cough (RCC) and idiopathic chronic cough (ICC), and as described herein.

In one embodiment, the kit further comprises one or more (e.g., 1, 2, 3, 4) additional therapeutic agents, as described herein.

The written instructions may also include a list of specific indications for which the compound is a suitable treatment.

Chronic Cough

As used herein, the term "chronic cough" (CC) refers to a cough lasting for more than about 8 weeks in adults, or for more than about 4 weeks in children.

Chronic cough is often considered to be a symptom of an associated condition.

In some cases, an associated condition that could cause chronic cough can be identified (i.e., explained chronic cough). Common causes of chronic cough are, for example, asthma, eosinophilic bronchitis, post-nasal drip syndrome (PNDS), gastro-oesophageal reflux disease (GORD), bronchiectasis chronic obstructive pulmonary disease (COPD), and idiopathic pulmonary fibrosis (IPF).

In other cases, an associated condition cannot be identified (i.e., unexplained or idiopathic chronic cough).

In some cases, the associated condition can be identified, and is treated, and chronic cough is improved following treatment of the associated condition.

In other cases, the associated condition that could cause chronic cough can be identified, and is treated, but chronic cough persists despite treatment of the associated condition. Here, the persistent chronic cough may be considered to be refractory chronic cough (i.e., refractory to treatment of the associated condition) or idiopathic chronic cough (i.e., the cause remains unexplained). This persistent chronic cough, whether described as idiopathic chronic cough or refractory chronic cough, can be considered to be a condition in its own right, rather than merely a symptom.

Therefore, a chronic cough-dedicated therapy can be used to improve the condition of chronic cough patients: with no identified associated condition (idiopathic chronic cough); with an identified associated condition causing the chronic cough but which cannot be treated; with an associated condition causing chronic cough which can be treated, but with a chronic cough refractory to treatment of the associated condition (refractory chronic cough).

In many cases, idiopathic/refractory chronic cough has a recognisable origin or history, for example, an earlier condition with chronic cough as a symptom which, despite treatment of the condition, gave rise to persistent chronic cough. This persistent chronic cough is usually independent of the earlier condition, and instead is often associated with neurological changes that arose concurrently with or subsequent to the earlier treatment.

For example, consider two patients with chronic cough as a symptom. Both are correctly diagnosed with asthma (the associated condition). Both are treated for their asthma (the associated condition). For both patients, most of the asthma symptoms are improved. However, for the first patient, chronic cough is improved, whereas for the second patient, it is not. This second patient, who was initially considered to have explained chronic cough (due to asthma) is now diagnosed with refractory chronic cough (because it is refractory to the treatment of the associated condition, asthma) or idiopathic chronic cough (because, now, the associated condition causing the persistent chronic cough is unknown, or not yet known).

In one embodiment, the treatment is treatment of chronic cough.

In one embodiment, the chronic cough is explained chronic cough.

In one embodiment, the chronic cough is chronic cough as a symptom of, associated with, or caused by: a diagnosed condition.

In one embodiment, the chronic cough is chronic cough as a symptom of, associated with, or caused by: a diagnosed cough-related condition.

In one embodiment, the chronic cough is chronic cough as a symptom of, associated with, or caused by: asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

In one embodiment, the chronic cough is idiopathic chronic cough (ICC).

In one embodiment, the chronic cough is refractory chronic cough (RCC).

In one embodiment, the chronic cough is refractory chronic cough (RCC) that persists after assessment and treatment of a cough-related condition, e.g., according to an accepted guideline.

In one embodiment, the chronic cough is refractory chronic cough (RCC) that persists after assessment and treatment of: asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF), e.g., according to an accepted guideline.

In one embodiment, the chronic cough (including, e.g., idiopathic chronic cough and refractory chronic cough) is a symptom of, associated with, or caused by: allotussia.

In one embodiment, the chronic cough (including, e.g., idiopathic chronic cough and refractory chronic cough) is a symptom of, associated with, or caused by: hypertussia.

In one embodiment, the chronic cough (including, e.g., idiopathic chronic cough and refractory chronic cough) is a symptom of, associated with, or caused by: cough hypersensitivity syndrome (CHS).

In one embodiment, the chronic cough (including, e.g., idiopathic chronic cough and refractory chronic cough) is a symptom of, associated with, or caused by: cough hypersensitivity reflex (CHR).

In one embodiment, the chronic cough (including, e.g., idiopathic chronic cough and refractory chronic cough) is a symptom of, associated with, or caused by: laryngeal paraesthesia.

In one embodiment, the chronic cough (including, e.g., idiopathic chronic cough and refractory chronic cough) is a symptom of, associated with, or caused by: laryngeal hypersensitivity syndrome (LHS).

In one embodiment, the chronic cough (including, e.g., idiopathic chronic cough and refractory chronic cough) is sensory neuropathic cough.

In one embodiment, the chronic cough (including, e.g., idiopathic chronic cough and refractory chronic cough) is a symptom of, associated with, or caused by: peripheral sensitization; central sensitization (cough centre); and/or cortical and/or subcortical maladaptive plasticity.

In one embodiment, the chronic cough (including, e.g., idiopathic chronic cough and refractory chronic cough) is a symptom of, associated with, or caused by: vagal neuropathy.

In one embodiment, the chronic cough (including, e.g., idiopathic chronic cough and refractory chronic cough) is a symptom of, associated with, or caused by: airway inflammation.

In one embodiment, the chronic cough (including, e.g., idiopathic chronic cough and refractory chronic cough) is a symptom of, associated with, or caused by: neurogenic inflammation and/or neuroinflammation.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, treatment of chronic cough (including, e.g., treatment of refractory chronic cough) includes the prophylaxis of cough, reducing the incidence of cough (e.g., urge-to-cough), reducing the frequency of cough (e.g., cough frequency), reducing the severity of cough (e.g., cough severity), alleviating the symptoms of cough (e.g., reducing throat irritation), etc.

In one embodiment, the treatment is to reduce one or more or all of: cough frequency, cough severity, urge-to-cough, and throat irritation.

In one embodiment, the treatment is to reduce cough frequency.

In one embodiment, the treatment is to reduce hourly cough frequency.

In one embodiment, the treatment is to reduce median hourly cough frequency.

In one embodiment, the treatment is to reduce mean hourly cough frequency.

In one embodiment, the treatment is to reduce awake hourly cough frequency.

In one embodiment, the treatment is to reduce awake median hourly cough frequency.

In one embodiment, the treatment is to reduce awake mean hourly cough frequency.

In one embodiment, the treatment is to reduce asleep hourly cough frequency.

In one embodiment, the treatment is to reduce asleep median hourly cough frequency.

In one embodiment, the treatment is to reduce asleep mean hourly cough frequency.

In one embodiment, the treatment is to reduce cough severity.

In one embodiment, the treatment is to reduce urge-to-cough.

In one embodiment, the treatment is to reduce throat irritation.

In one embodiment, the treatment reduces cough frequency.

In one embodiment, the treatment reduces hourly cough frequency.

In one embodiment, the treatment reduces median hourly cough frequency.

In one embodiment, the treatment reduces mean hourly cough frequency.

In one embodiment, the treatment reduces awake hourly cough frequency.

In one embodiment, the treatment reduces awake median hourly cough frequency.

In one embodiment, the treatment reduces awake mean hourly cough frequency.

In one embodiment, the treatment reduces asleep hourly cough frequency.

In one embodiment, the treatment reduces asleep median hourly cough frequency.

In one embodiment, the treatment reduces asleep mean hourly cough frequency.

In one embodiment, the treatment reduces cough severity.

In one embodiment, the treatment reduces urge-to-cough.

In one embodiment, the treatment reduces throat irritation.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Routes of Administration

The compound, [((1R,2S,5R)-2-isopropyl-5-methyl-cyclohexanecarbonyl)-amino]-acetic acid isopropyl ester (also referred to herein as "AX-8" or "Gly-O-iPr"), as described herein, or pharmaceutical composition comprising the compound may be administered to a subject by any convenient route of administration, whether systemically/peripherally or topically (i.e., at the site of desired action).

In one preferred embodiment, the route of administration is topical.

Routes of administration include: oral (e.g., by ingestion); oromucosal; buccal (e.g., between the gums and cheek); sublingual (e.g., under the tongue); transdermal (including, e.g., by a patch, plaster, etc.); transmucosal (including, e.g., by a patch, plaster, etc.); intranasal (e.g., by nasal spray, drops or from an atomiser or dry powder delivery device); pulmonary (e.g., by inhalation or insufflation therapy using, e.g., an aerosol, e.g., through the mouth or nose).

In one preferred embodiment, the route of administration is oral.

In one preferred embodiment, the route of administration is topical oral.

In one preferred embodiment, the route of administration is oromucosal.

In one preferred embodiment, the route of administration is topical oromucosal.

In one preferred embodiment, the route of administration is buccal.

In one preferred embodiment, the route of administration is topical buccal.

In one preferred embodiment, the route of administration is sublingual.

In one preferred embodiment, the route of administration is topical sublingual.

In one preferred embodiment, the route of administration is intranasal.

In one preferred embodiment, the route of administration is topical intranasal.

In one preferred embodiment, the route of administration is transmucosal.

In one preferred embodiment, the route of administration is topical transmucosal.

Dosage

It will be appreciated by one of skill in the art that an appropriate dosage of the compound, [((1R,2S,5R)-2-isopropyl-5-methyl-cyclohexanecarbonyl)-amino]-acetic acid isopropyl ester (also referred to herein as "AX-8" or "Gly-O-iPr"), as described herein, or composition comprising the compound, can vary from patient to patient. Determining the optimal dosage will generally involve the balancing of the level of therapeutic benefit against any risk or deleterious side effects. The selected dosage level will depend on a variety of factors including the activity of the compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In one embodiment, the dose is in the range of from about 1 µg to about 5 mg of the compound per kilogram body weight of the subject per day.

In one embodiment, the dose is in the range of from about 5 µg to about 2 mg of the compound per kilogram body weight of the subject per day.

In one embodiment, the dose is in the range of from about 15 µg to about 0.7 mg of the compound per kilogram body weight of the subject per day.

In one embodiment, the dose is in the range of from about 30 µg to about 0.4 mg of the compound per kilogram body weight of the subject per day.

In one embodiment, the dose is in the range of from about 70 µg to about 0.3 mg of the compound per kilogram body weight of the subject per day.

Similarly, in one embodiment, the dose is in the range of from about 0.07 mg to about 350 mg of the compound per day.

In one embodiment, the dose is in the range of from about 0.35 mg to about 140 mg of the compound per day.

In one embodiment, the dose is in the range of from about 1 mg to about 50 mg of the compound per day.

In one embodiment, the dose is in the range of from about 2 mg to about 30 mg of the compound per day.

In one embodiment, the dose is in the range of from about 5 mg to about 20 mg of the compound per day.

Where the compound is a salt, an ester, an amide, a prodrug, or the like, the amount administered is calculated on the basis of the parent compound and so the actual weight to be used is increased proportionately.

Treatment Regimen

The compound, or pharmaceutical composition comprising the compound, may be administered according to any suitable treatment plan or regimen.

Mostly likely, administration will be performed by the patient, "on demand", according to the patient's needs. For example, the patient may be directed to self-administer the compound, or pharmaceutical composition comprising the compound, upon anticipation of cough (e.g., as prophylaxis); immediately following the start of cough; after a period of prolonged cough; etc.

As described herein, a single administration of a 5 mg ODT was found to have an efficacy that lasted for up to about 8 hours, and so it may be anticipated that 2 to 4 administrations daily may be sufficient.

In one embodiment, the treatment regimen is 1 to 5 administrations daily (i.e., administration one to five times daily).

In one embodiment, the treatment regimen is 1 to 4 administrations daily (i.e., administration one to four times daily).

In one embodiment, the treatment regimen is 2 to 5 administrations daily (i.e., administration two to five times daily).

In one embodiment, the treatment regimen is 2 to 4 administrations daily (i.e., administration two to four times daily).

In one embodiment, the treatment regimen is 2 administrations daily (i.e., administration twice daily).

In one embodiment, the treatment regimen is 3 administrations daily (i.e., administration three times daily).

In one embodiment, the treatment regimen is 4 administrations daily (i.e., administration four times daily).

In one embodiment, the treatment regimen is pro re nata (PRN) (e.g., as needed, as the situation arises, etc.).

Formulations

While it is possible for the compound, [((1R,2S,5R)-2-isopropyl-5-methyl-cyclohexanecarbonyl)-amino]-acetic acid isopropyl ester (also referred to herein as "AX-8" or "Gly-O-iPr"), as described herein, to be administered alone, it is preferable to present it as a pharmaceutical formulation (e.g., composition, preparation, medicament) comprising the compound, as described herein, together with one or more other pharmaceutically acceptable ingredients well known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Described herein are pharmaceutical compositions and methods of making a pharmaceutical composition comprising admixing the compound together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, tinctures, gels, pastes, ointments, creams, lotions, oils, foams, sprays, mists, or aerosols.

In one embodiment, the compound is formulated as a spray.

In one embodiment, the compound is formulated as a mist.

In one embodiment, the compound is formulated as an aerosol.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, and boluses.

In one embodiment, the compound is formulated as a tablet.

In one embodiment, the compound is formulated as an orally disintegrating tablet (ODT), also referred to as an orodispersible tablet, a mouth-dissolving tablet, a rapid-dissolving tablet, a fast-disintegrating tablet, or a fast-dissolving tablet. ODT's, as contemplated herein, are pharmaceutical dosage forms that disintegrate in saliva within a few minutes of topical application on the surface of the tongue. Preferably, the disintegration time is long enough to permit the compound to cover the mucosa. Key advantages of the use of ODT's to deliver the compound are the ease of administration (e.g., oral administration) and delivery to the site of action (e.g., topical rather than system).

A typical ODT is composed predominantly of an inert vehicle, diluent, or carrier. The medicinal agent (i.e., AX-8) is interspersed within this carrier. The ODT will dissolve when placed on the dorsal surface of the tongue thereby releasing the medicinal agent so that it may come in contact with the tissues of the lower oropharynx (LRO). A typical diluent, carrier, or vehicle may be a "polyhydric alcohol" construed as describing the following substances: xylitol, mannitol, sorbitol, maltitol, isomaltitol, maltotriitol, lactitol, and β-linked-glucopyranasido-sorbitol. Flavoring agents such as the sweeteners, aspartame, sucralose, or alitame, may be added to mask any tastes. Typically, the mix is granulated to a uniformly dispersed blend; dispersing agents, anti-caking agents, and/or lubricants may be added; and the mixture is then compressed to form the ODT. As an example, ODT used in the studied described herein contained Ludiflash® (Mannitol, Kollidon® CL-SF, Kollicoat® SR 30D), sorbitol, silica colloidal anhydrous, and magnesium stearate.

In one embodiment, the compound is formulated as an ODT containing from about 0.5 mg to about 50 mg of the compound.

In one embodiment, the compound is formulated as an ODT containing from about 1 to about 30 mg of the compound.

In one embodiment, the compound is formulated as an ODT containing from about 2 to about 20 mg of the compound.

In one embodiment, the compound is formulated as an ODT containing from about 2 to about 10 mg of the compound.

In one embodiment, the compound is formulated as an ODT containing about 5 mg of the compound.

In one embodiment, the compound is formulated as an ODT containing from about 50 mg to about 250 mg of the compound.

Where the compound is a salt, an ester, an amide, a prodrug, or the like, the amount administered is calculated on the basis of the parent compound and so the actual weight to be used is increased proportionately.

Formulations suitable for buccal administration include mouthwashes, lozenges, pastilles, as well as patches, adhesive plasters, depots, and reservoirs. Lozenges typically comprise the compound in a flavoured basis, usually sucrose and acacia or tragacanth.

Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, sprays, mists, lozenges, pastilles, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

In one embodiment, the compound is formulated as an aerosol spray.

Combination Therapies

The term "treatment" includes combination treatments and therapies, in which two or more treatments or therapies are combined, for example, sequentially or simultaneously. For example, the compound, [((1R,2S,5R)-2-isopropyl-5-methyl-cyclohexanecarbonyl)-amino]-acetic acid isopropyl ester (also referred to herein as "AX-8" or "Gly-O-iPr"), as described herein, may also be used in combination therapies, e.g., in conjunction with other agents, for example, one or more antitussive agents, expectorants, mucolytics, decongestants, nasal decongestants, first generation antihistamines, antihistamines, opioid analgesics, non-opiate analgesics, antipyretics, etc., and combinations thereof.

The particular combination would be at the discretion of the physician who would select dosages using his common general knowledge and dosing regimens known to a skilled practitioner.

The agents (i.e., the compound, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound, plus one or more other agents) may be formulated together in a single dosage form, or alternatively, the individual agents may be formulated separately and presented together in the form of a kit, optionally with instructions for their use.

The Subject/Patient

The subject/patient may be a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

In one preferred embodiment, the subject/patient is a human.

Compounds Configured for Use in Treatment of Chronic Cough

Also described herein is a compound comprising: [((1R,2S,5R)-2-isopropyl-5-methyl-cyclohexanecarbonyl)-amino]-acetic acid isopropyl ester, or a pharmaceutically acceptable salt, hydrate, or solvate thereof configured for use in treatment of chronic cough.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of explained chronic cough.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough as a symptom of, associated with, or caused by a diagnosed condition.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough as a symptom of, associated with, or caused by a diagnosed cough-related condition.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough as a symptom of, associated with, or caused by asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of idiopathic chronic cough (ICC).

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of refractory chronic cough (RCC).

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of refractory chronic cough (RCC) that persists after assessment and treatment of a cough-related condition.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of refractory chronic cough (RCC) that persists after assessment and treatment of: asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by allotussia.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by hypertussia.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by cough hypersensitivity syndrome (CHS).

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough is a symptom of, associated with, or caused by cough hypersensitivity reflex (CHR).

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by laryngeal paraesthesia.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by laryngeal hypersensitivity syndrome (LHS).

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being sensory neuropathic cough.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by peripheral sensitization; central sensitization (cough centre); and/or cortical and/or subcortical maladaptive plasticity.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by vagal neuropathy.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by airway inflammation.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment of the chronic cough being a symptom of, associated with, or caused by neurogenic inflammation and/or neuroinflammation.

In one embodiment, the wherein the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for use in treatment to:
  reduce cough frequency;
  reduce hourly cough frequency;
  reduce median hourly cough frequency;
  reduce mean hourly cough frequency;
  reduce awake hourly cough frequency;
  reduce awake median hourly cough frequency;
  reduce awake mean hourly cough frequency;
  reduce asleep hourly cough frequency;
  reduce asleep median hourly cough frequency;
  reduce asleep mean hourly cough frequency;
  reduce cough severity;
  reduce urge-to-cough; and/or
  reduce throat irritation.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for:
  topical oral administration of the compound;
  topical oromucosal administration of the compound;
  topical buccal administration of the compound;
  topical sublingual administration of the compound;
  topical intranasal administration of the compound; or
  topical transmucosal administration of the compound.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for:
  a dose in the range of from about 1 μg to about 5 mg of the compound per kilogram body weight per day;
  a dose in the range of from about 5 μg to about 2 mg of the compound per kilogram body weight per day;
  a dose in the range of from about 15 μg to about 0.7 mg of the compound per kilogram body weight per day;
  a dose in the range of from about 30 μg to about 0.4 mg of the compound per kilogram body weight per day; or
  a dose in the range of from about 70 μg to about 0.3 mg of the compound per kilogram body weight per day.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for:
  a dose in the range of from about 0.07 mg to about 350 mg of the compound per day;
  a dose in the range of from about 0.35 mg to about 140 mg of the compound per day;
  a dose in the range of from about 1 mg to about 50 mg of the compound per day;
  a dose in the range of from about 2 mg to about 30 mg of the compound per day; or
  a dose in the range of from about 5 mg to about 20 mg of the compound per day.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for:
  a treatment regimen of 1 to 5 administrations daily;
  a treatment regimen of 1 to 4 administrations daily;
  a treatment regimen of 2 to 5 administrations daily;
  a treatment regimen of 2 to 4 administrations daily;
  a treatment regimen of 2 administrations daily;
  a treatment regimen of 3 administrations daily; or
  a treatment regimen of 4 administrations daily.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured for a pro re nata (PRN) treatment regimen.

In one embodiment, the [((1R,2S,5R)-2-isopropyl-5-methyl-cyclohexanecarbonyl)-amino]-acetic acid isopropyl ester, or the pharmaceutically acceptable salt, hydrate, or solvate thereof is configured as:
  a tablet;
  an orally disintegrating tablet (ODT);
  a spray;
  a mist; or
  an aerosol.

Methods of Manufacturing a Medicament

Also described herein is a method of manufacturing a medicament, the method comprising:
  preparing a medicament for the treatment of chronic cough having a compound that is [((1R,2S,5R)-2-isopropyl-5-methyl-cyclohexanecarbonyl)-amino]-acetic acid isopropyl ester, or a pharmaceutically acceptable salt, hydrate, or solvate thereof.

In one embodiment, the preparing the medicament having the compound comprises preparing the medicament having the compound for the treatment of explained chronic cough.

In one embodiment, the preparing the medicament having the compound comprises preparing the medicament having the compound for the treatment of the chronic cough as a symptom of, associated with, or caused by a diagnosed condition.

In one embodiment, the preparing the medicament having the compound comprises preparing the medicament having the compound for the treatment of the chronic cough as a symptom of, associated with, or caused by a diagnosed cough-related condition.

In one embodiment, the preparing the medicament having the compound comprises preparing the medicament having the compound for the treatment of the chronic cough as a symptom of, associated with, or caused by asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

In one embodiment, the preparing the medicament having the compound comprises preparing the medicament having the compound for the treatment of idiopathic chronic cough (ICC).

In one embodiment, the preparing the medicament having the compound comprises preparing the medicament having the compound for the treatment of refractory chronic cough (RCC).

In one embodiment, the preparing the medicament having the compound comprises preparing the medicament having the compound for the treatment of refractory chronic cough (RCC) that persists after assessment and treatment of a cough-related condition.

In one embodiment, the preparing the medicament having the compound comprises preparing the medicament having the compound for the treatment of refractory chronic cough (RCC) that persists after assessment and treatment of: asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

In one embodiment, the preparing the medicament having the compound comprises preparing the medicament having the compound for the treatment of the chronic cough being a symptom of, associated with, or caused by allotussia.

In one embodiment, the preparing the medicament having the compound comprises preparing the medicament having the compound for the treatment of the chronic cough being a symptom of, associated with, or caused by hypertussia.

In one embodiment, the preparing the medicament having the compound comprises preparing the medicament having the compound for the treatment of the chronic cough being a symptom of, associated with, or caused by cough hypersensitivity syndrome (CHS).

In one embodiment, the preparing the medicament having the compound comprises preparing the medicament having the compound for the treatment of the chronic cough is a symptom of, associated with, or caused by cough hypersensitivity reflex (CHR).

In one embodiment, the preparing the medicament having the compound comprises preparing the medicament having the compound for the treatment of the chronic cough being a symptom of, associated with, or caused by laryngeal paraesthesia.

In one embodiment, the preparing the medicament having the compound comprises preparing the medicament having the compound for the treatment of the chronic cough being a symptom of, associated with, or caused by laryngeal hypersensitivity syndrome (LHS).

In one embodiment, the preparing the medicament having the compound comprises preparing the medicament having the compound for the treatment of the chronic cough being sensory neuropathic cough.

In one embodiment, the preparing the medicament having the compound comprises preparing the medicament having the compound for the treatment of the chronic cough being a symptom of, associated with, or caused by peripheral sensitization; central sensitization (cough centre); and/or cortical and/or subcortical maladaptive plasticity.

In one embodiment, the preparing the medicament having the compound comprises preparing the medicament having the compound for the treatment of the chronic cough being a symptom of, associated with, or caused by vagal neuropathy.

In one embodiment, the preparing the medicament having the compound comprises preparing the medicament having the compound for the treatment of the chronic cough being a symptom of, associated with, or caused by airway inflammation.

In one embodiment, the preparing the medicament having the compound comprises preparing the medicament having the compound for the treatment of the chronic cough being a symptom of, associated with, or caused by neurogenic inflammation and/or neuroinflammation.

In one embodiment, the preparing the medicament having the compound comprises preparing the medicament having the compound to:
  reduce cough frequency;
  reduce hourly cough frequency;
  reduce median hourly cough frequency;
  reduce mean hourly cough frequency;
  reduce awake hourly cough frequency;
  reduce awake median hourly cough frequency;
  reduce awake mean hourly cough frequency;
  reduce asleep hourly cough frequency;
  reduce asleep median hourly cough frequency;
  reduce asleep mean hourly cough frequency;
  reduce cough severity;
  reduce urge-to-cough; and/or
  reduce throat irritation.

In one embodiment, the preparing the medicament having the compound comprises preparing the medicament for:
  topical oral administration of the compound;
  topical oromucosal administration of the compound;
  topical buccal administration of the compound;
  topical sublingual administration of the compound;
  topical intranasal administration of the compound; or
  topical transmucosal administration of the compound.

In one embodiment, the preparing the medicament having the compound comprises preparing the medicament having the compound as:
  a dose in the range of from about 1 μg to about 5 mg of the compound per kilogram body weight per day;
  a dose in the range of from about 5 μg to about 2 mg of the compound per kilogram body weight per day;
  a dose in the range of from about 15 μg to about 0.7 mg of the compound per kilogram body weight per day;
  a dose in the range of from about 30 μg to about 0.4 mg of the compound per kilogram body weight per day; or
  a dose in the range of from about 70 μg to about 0.3 mg of the compound per kilogram body weight per day.

In one embodiment, the preparing the medicament having the compound comprises preparing the medicament having the compound as:
  a dose in the range of from about 0.07 mg to about 350 mg of the compound per day;
  a dose in the range of from about 0.35 mg to about 140 mg of the compound per day;
  a dose in the range of from about 1 mg to about 50 mg of the compound per day;
  a dose in the range of from about 2 mg to about 30 mg of the compound per day; or
  a dose in the range of from about 5 mg to about 20 mg of the compound per day.

In one embodiment, the preparing the medicament having the compound comprises preparing the medicament having the compound as:
  a treatment regimen of 1 to 5 administrations daily;
  a treatment regimen of 1 to 4 administrations daily;
  a treatment regimen of 2 to 5 administrations daily;
  a treatment regimen of 2 to 4 administrations daily;
  a treatment regimen of 2 administrations daily;
  a treatment regimen of 3 administrations daily; or
  a treatment regimen of 4 administrations daily.

In one embodiment, the preparing the medicament having the compound comprises preparing the medicament having the compound as a pro re nata (PRN) treatment regimen.

In one embodiment, the preparing the medicament having the compound comprises preparing the medicament having the compound as:
  a tablet;
  an orally disintegrating tablet (ODT);
  a spray;
  a mist; or
  an aerosol.

Methods of Treatment of Chronic Cough

Also described herein is a method of treatment of chronic cough in a patient, the method comprising:
  administering to the patient in need of treatment of chronic cough a therapeutically effective amount of a compound that is [((1R,2S,5R)-2-isopropyl-5-methyl-cyclohexanecarbonyl)-amino]-acetic acid isopropyl ester, or a pharmaceutically acceptable salt, hydrate, or solvate thereof.

In one embodiment, the administering step comprises administering the compound to a patient in need of treatment of explained chronic cough.

In one embodiment, the administering step comprises administering the compound to a patient in need of treatment of the chronic cough as a symptom of, associated with, or caused by a diagnosed condition.

In one embodiment, the administering step comprises administering the compound to a patient in need of treatment of the chronic cough as a symptom of, associated with, or caused by a diagnosed cough-related condition.

In one embodiment, the administering step comprises administering the compound to a patient in need of treatment of the chronic cough as a symptom of, associated with, or caused by asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

In one embodiment, the administering step comprises administering the compound to a patient in need of treatment of idiopathic chronic cough (ICC).

In one embodiment, the administering step comprises administering the compound to a patient in need of treatment of refractory chronic cough (RCC).

In one embodiment, the administering step comprises administering the compound to a patient in need of treatment of refractory chronic cough (RCC) that persists after assessment and treatment of a cough-related condition.

In one embodiment, the administering step comprises administering the compound to a patient in need of treatment of refractory chronic cough (RCC) that persists after assessment and treatment of: asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

In one embodiment, the administering step comprises administering the compound to a patient in need of treatment of the chronic cough being a symptom of, associated with, or caused by allotussia.

In one embodiment, the administering step comprises administering the compound to a patient in need of treatment of the chronic cough being a symptom of, associated with, or caused by hypertussia.

In one embodiment, the administering step comprises administering the compound to a patient in need of treatment of the chronic cough being a symptom of, associated with, or caused by cough hypersensitivity syndrome (CHS).

In one embodiment, the administering step comprises administering the compound to a patient in need of treatment of the chronic cough being a symptom of, associated with, or caused by cough hypersensitivity reflex (CHR).

In one embodiment, the administering step comprises administering the compound to a patient in need of treatment of the chronic cough being a symptom of, associated with, or caused by laryngeal paraesthesia.

In one embodiment, the administering step comprises administering the compound to a patient in need of treatment of the chronic cough being a symptom of, associated with, or caused by laryngeal hypersensitivity syndrome (LHS).

In one embodiment, the administering step comprises administering the compound to a patient in need of treatment of the chronic cough being sensory neuropathic cough.

In one embodiment, the administering step comprises administering the compound to a patient in need of treatment of the chronic cough being a symptom of, associated with, or caused by peripheral sensitization; central sensitization (cough centre); and/or cortical and/or subcortical maladaptive plasticity.

In one embodiment, the administering step comprises administering the compound to a patient in need of treatment of the chronic cough being a symptom of, associated with, or caused by vagal neuropathy.

In one embodiment, the administering step comprises administering the compound to a patient in need of treatment of the chronic cough being a symptom of, associated with, or caused by airway inflammation.

In one embodiment, the administering step comprises administering the compound to a patient in need of treatment of the chronic cough being a symptom of, associated with, or caused by neurogenic inflammation and/or neuroinflammation.

In one embodiment, the administering step comprises administering the compound to a patient to:
  reduce cough frequency;
  reduce hourly cough frequency;
  reduce median hourly cough frequency;
  reduce mean hourly cough frequency;
  reduce awake hourly cough frequency;
  reduce awake median hourly cough frequency;
  reduce awake mean hourly cough frequency;
  reduce asleep hourly cough frequency;
  reduce asleep median hourly cough frequency;
  reduce asleep mean hourly cough frequency;
  reduce cough severity;
  reduce urge-to-cough; and/or
  reduce throat irritation.

In one embodiment, the administering step comprises administering the compound to a patient in need of treatment via:
  topical oral administration of the compound;
  topical oromucosal administration of the compound;
  topical buccal administration of the compound;
  topical sublingual administration of the compound;
  topical intranasal administration of the compound; or
  topical transmucosal administration of the compound.

In one embodiment, the administering step comprises administering the compound to a patient in need of treatment as:
  a dose in the range of from about 1 μg to about 5 mg of the compound per kilogram body weight per day;
  a dose in the range of from about 5 μg to about 2 mg of the compound per kilogram body weight per day;
  a dose in the range of from about 15 μg to about 0.7 mg of the compound per kilogram body weight per day;
  a dose in the range of from about 30 μg to about 0.4 mg of the compound per kilogram body weight per day; or
  a dose in the range of from about 70 μg to about 0.3 mg of the compound per kilogram body weight per day.

In one embodiment, the administering step comprises administering the compound to a patient in need of treatment as:
  a dose in the range of from about 0.07 mg to about 350 mg of the compound per day;
  a dose in the range of from about 0.35 mg to about 140 mg of the compound per day;
  a dose in the range of from about 1 mg to about 50 mg of the compound per day;
  a dose in the range of from about 2 mg to about 30 mg of the compound per day; or
  a dose in the range of from about 5 mg to about 20 mg of the compound per day.

In one embodiment, the administering step comprises administering the compound to a patient in need of treatment as:

a treatment regimen of 1 to 5 administrations daily;
a treatment regimen of 1 to 4 administrations daily;
a treatment regimen of 2 to 5 administrations daily;
a treatment regimen of 2 to 4 administrations daily;
a treatment regimen of 2 administrations daily;
a treatment regimen of 3 administrations daily; or
a treatment regimen of 4 administrations daily.

In one embodiment, the administering step comprises administering the compound to a patient in need of treatment as a pro re nata (PRN) treatment regimen.

In one embodiment, the administering step comprises administering the compound to a patient in need of treatment as:
a tablet;
an orally disintegrating tablet (ODT);
a spray;
a mist; or
an aerosol.

Clinical Trial 1

A first clinical trial for the use of the compound, [((1R, 2S,5R)-2-isopropyl-5-methyl-cyclohexanecarbonyl)-amino]-acetic acid isopropyl ester (also referred to herein as "AX-8" or "Gly-O-iPr"), for the treatment of RCC was started, but was prematurely ended. Basic details of the trial are set out in the following table.

Currently, some details may be seen online at: https://www.clinicaltrialsregister.eu/ctr-search/trial/2016-004803-30/GB

TABLE 1

| First Clinical Trial | |
|---|---|
| EudraCT number | 2016-004803-30 |
| National Competent Authority | UK-MHRA |
| Date on which this record was first entered in the EudraCT database | 2017 Jan. 19 |
| Full title of the trial | A multi-centre, randomised, placebo and active-controlled, double-blind, cross-over, phase IIa proof-of-concept trial to investigate the efficacy and safety of AX-8 Tablets 5 mg in patients with chronic refractory cough and associated upper airway symptoms |
| INN - Proposed INN | Recommended International Nonproprietary Name (rINN): [(1 R, 2S, 5R)-5-Methyl-2-isopropyl cyclohexane carbonyl]aminoacetic acid isopropylester |
| Medical condition(s) being investigated | Chronic refractory cough and associated upper airway symptoms |
| Main objective of the trial | The primary research question is to study the efficacy of AX-8 Tablets 5 mg in suppressing cough in patients with chronic refractory cough and associated upper airway symptoms when compared to 5 mg menthol (active comparator) and placebo. As assessed by measuring the changes from baseline in cough frequency over 8 hours (4 hours after intake of 1st dose and 4 hours after intake of 2nd dose) for AX-8, menthol and placebo. |

Clinical Trial 2

A second clinical trial (open-label Phase IIa) for the use of the compound, [((1R,2S,5R)-2-isopropyl-5-methyl-cyclohexanecarbonyl)-amino]-acetic acid isopropyl ester (also referred to herein as "AX-8" or "Gly-O-iPr"), for the treatment of RCC has just been completed. Basic details of the trial are set out in the following table.

Currently, some details may be seen online at: https://www.clinicaltrialsregister.eu/ctr-search/trial/2017-003108-27/GB

TABLE 2

| Second Clinical Trial | |
|---|---|
| EudraCT number | 2017-003108-27 |
| National CompetentAuthority | UK-MHRA |
| Date on which this record was first entered in the EudraCT database | 2017 Aug. 31 |
| Full title of the trial | A pilot study of the efficacy, safety, and tolerability of AX-8 for the treatment of refractory chronic cough |
| Other descriptive name | Gly-O-iPr, [((1R, 2S, 5R)-2-isopropyl-5-methyl-cyclohexanecarbonyl)-amino]-acetic acid isopropyl ester |
| Pharmaceutical form | Orodispersible tablet |
| Route of administration | Oromucosal use |
| Strength | 5 mg |

TABLE 2-continued

| Second Clinical Trial | |
| --- | --- |
| Medical condition(s) being investigated | Refractory Chronic Cough (RCC). |
| Main objective of the trial | To assess the effectiveness of AX-8 for the treatment of RCC and associated upper airway symptoms after one dose of treatment in reducing awake cough frequency compared to baseline, for the purpose of planning a future randomised controlled trial. |

Upon completion of the second clinical trial (described in detail below), the compound was found to have unexpected antitussive properties in patients with RCC, decreasing awake hourly cough frequency, throat irritation, urge-to-cough, and cough severity. No compound-related adverse effects were observed.

As demonstrated in the clinical trial, a 5 mg dose of the compound improves cough in RCC patients by decreasing cough frequency and also visual analog scale (VAS) scores for all of the coughing characteristics assessed (i.e., cough severity, urge to cough, throat irritation).

This is unexpected because MK-7264 (also known as AF-219 and Gefapixant), the more advanced RCC drug currently under development (Phase 3 clinical trials started March 2018) is efficient in reducing cough frequency but poorly effective in improving the VAS scores in RCC patients (see, e.g., Abdulqawi et al., 2015; Smith et al., 2017a; Smith et al., 2017b; Smith et al., 2020). Cough severity was improved significantly only for doses of 50 mg and 1200 mg per day with respectively adverse events related to taste (i.e., dysgeusia, hypogeusia, or ageusia) in 81% and 100% of patients. Urge-to-cough was shown to be improved significantly only with the 1200 mg per day dose. Phase 3 clinical trials (NCT03449134 and NCT03449147, still ongoing in June 2020) are studying 15 mg and 45 mg doses of MK-7264.

AX-8 is the only compound which has been shown to decrease throat irritation in RCC patients.

Study Objectives

AX-8 bioavailability and safety have been previously addressed in a Phase 1 study in healthy human subjects. However, until now, AX-8 has not been studied in patients with chronic cough (CC). This study was a pilot study of the efficacy, safety, and tolerability of AX-8 for the treatment of Refractory chronic cough (RCC).

The primary objective of the study was to assess the effectiveness of AX-8 (the study drug) for the treatment of RCC and associated upper airway symptoms after one dose of treatment (an orally disintegrating tablet (ODT) having 5 mg AX-8, administered orally and dissolved on the tongue) in reducing awake cough frequency compared to baseline, for the purpose of planning a future randomized controlled trial.

A secondary objective of the study was to evaluate the duration of effectiveness of AX-8 after 1 dose of treatment in reducing hourly objective cough frequency over a 24-hour monitoring period.

An additional secondary objective of the study was to evaluate the effectiveness of AX-8 in: (a) reducing the cough severity measured by a Visual Analog Scale (VAS); (b) reducing the throat irritation and the urge-to-cough (VAS); (c) inducing a sensation of throat cooling (VAS).

An additional secondary objective of the study was to assess the safety and tolerability of AX-8 treatment in patients with RCC.

An exploratory objective (added to the study after initiation) was to evaluate the pharmacokinetic (PK) profile of AX-8.

Ethics, Approval and Location

The study protocol including all relevant documents were reviewed and approved by the appropriate independent ethics committees. The study was performed in accordance with the current version of the declaration of Helsinki (52$^{nd}$ WMA General Assembly, Edinburgh, Scotland, October 2000). The study was conducted in agreement with the International Conference on Harmonisation (ICH) guidelines on Good Clinical Practice (GCP). The study was performed in compliance with the requirements of the Medicines and Healthcare products Regulatory Agency (MHRA). All patients provided written informed consent (ICF) to participate in the study prior to being screened. The study was conducted at NIHR Manchester Clinical Research Facility (CRF), Manchester University NHS Foundation Trust (MFT), Southmoor Rd, Wythenshawe, Manchester M23 9LT, UK.

Study Timing

The study consisted of five periods, for a total study period of approximately 4 weeks:

Table 3

Visit Summary

| Period | Visit | Visit Schedule |
| --- | --- | --- |
| Screening | Visit 1 ("Screening Visit") | Day −14 to −1 |
| Baseline | Visit 2 ("Baseline Visit") | Day 0 |
| Treatment | Visit 3 ("Treatment Visit") | Day 1 |
|  | Visit 4 ("Follow-Up Visit") | Day 2 |
| End of Study | Visit 5 ("End of Study Visit") | Day 7 to 14 |

During the screening period, subjects underwent eligibility evaluation and were enrolled.

At Day 0 (Visit 2; Baseline Visit), eligible subjects had cough monitoring conducted over 24 hours and urge-to-cough (UTC), cough severity, and throat irritation were assessed separately using VAS over 4 hours in the clinic and followed up with a patient diary at home.

Subjects were required to fast overnight (at least 8 hours) before the Day 0 visit. A breakfast was provided in the unit at least 30 minutes before subjects have the Cough Monitor installed. No food was permitted for 4 hours after the Cough Monitor was installed. Liquids were permitted until the time the Cough Monitor was installed and not permitted (including water) until 2 hours after the Cough Monitor was installed; after 2 hours, water only in a reasonable amount was permitted. After 4 hours, no food or liquid restrictions applied.

At Day 1 (Visit 3; Treatment Visit), eligible subjects received one 5 mg AX-8 ODT. Cough monitoring was conducted over 24 hours and different VAS for UTC, Cough Severity, Throat Irritation, Throat Cooling, and Taste Perception were assessed using VAS over 4 hours in the clinic after dosing and followed up with a patient diary at home.

Subjects were required to fast overnight (at least 8 hours) before the Day 1 visit. A breakfast was provided in the unit at least 30 minutes before subjects received the dose of AX-8. No food was permitted for 4 hours after dose administration. Liquids were permitted until the time of dose administration and not permitted until 2 hours after dosing (including water); after 2 hours, water only in a reasonable amount were permitted. After 4 hours, no food or liquid restrictions applied.

The primary efficacy endpoint was assessed after one day of treatment.

At Day 2 (Visit 4; Follow-Up Visit), the Cough Monitor was removed, and the patient diary returned.

Between 7-14 days after Day 1 (Visit 5; End of Study Visit), an end of study visit was performed.

Subjects who withdrew from the study after receiving the study drug and prior to completing the End of Study Visit were asked to complete an Early Withdrawal Visit (EWV), whereby the same procedures as for the End of Study Visit were performed.

Enrolment

Adult subjects with a history of RCC and associated upper airway symptoms (i.e., throat irritation/tickling associated with coughing episodes) were enrolled in the study.

Inclusion Criteria:

Subjects had to meet the following criteria to be enrolled into the study:

Females and males between 18 and 80 years of age inclusive.

Have a diagnosis of RCC or unexplained cough for at least one year (see British Thoracic Society (BTS) guidelines) and associated upper airway symptoms (throat or laryngeal irritation, tickling, dryness or discomfort) of at least 8-week duration. Regular pattern of cough with expected daily episodes of cough that occur throughout the day, as ascertained by medical history.

Chest radiograph or thorax computed tomography scan within the last 5 years not demonstrating any abnormality considered to be significantly contributing to the chronic cough in the opinion of the Principal Investigator and Medical Monitor.

At the Screening Visit, have a score of 40 mm on the Cough Severity VAS.

At the Baseline Visit, have a score of 40 mm on the Cough Severity VAS.

All female subjects who are of childbearing potential must practice highly effective contraception (i.e., pregnancy prevention method with a failure rate of <1% per year) from the time of the initial Screening visit until 4 weeks after last dose of study drug.

At the Baseline Visit, have a body mass index (BMI)<33 kg/m$^2$.

Be willing and able to comply with all aspects of the protocol.

Provided written informed consent.

Exclusion Criteria:

Subjects who met any of the following criteria were not eligible for participation in the study:

Prior treatment with AX-8.

Hypersensitivity or intolerance to AX-8 or other TRPM8 agonists (e.g., menthol, menthol-like compounds), or any of the excipients of AX-8 ODT.

Current smoker or individuals who have given up smoking within the past 12 months or ex-smoker with >20 pack-years.

Forced expiratory volume in one second (FEV1)/forced vital capacity (FVC) <60%.

History of upper or lower respiratory tract infection or recent significant change in pulmonary status within 4 weeks of the Baseline Visit.

History of cystic fibrosis.

History of opioid use within 1 week of the Baseline Visit if used for the treatment of RCC. Opioids, if required for other indications are permitted providing that subject is receiving a stable dose for at least 1 week prior to the Baseline Visit and are still experiencing a troublesome cough. Subjects must remain on a stable dose for the duration of the study until the Follow-Up Visit.

Requiring concomitant therapy with prohibited medications.

Treatment with biologic therapies within 8 weeks or 5 half-lives prior to the Baseline Visit, whichever is longer.

Treatment with any investigational therapy within 4 weeks prior to the Baseline Visit.

Clinically significant abnormality of hepatic function defined as total bilirubin, alanine aminotransferase (ALT) or aspartate aminotransferase (AST) >2× the upper limit of normal (ULN) during screening.

Clinically significant abnormality of renal function, defined as estimated glomerular filtration rate (eGFR) <60 ml/min.

Positive test for any drug-of-abuse (unless this can be explained by the subject's medication).

History of malignancy within 5 years prior to the Baseline Visit, with the exception of completely treated and non-metastatic basal cell carcinoma or squamous cell carcinoma of the skin.

History of a major psychiatric condition (including major depressive disorder, bipolar disorder, or schizophrenia), suicidal ideation, or suicide attempt.

Known active hepatitis infection.

Known history of human immunodeficiency virus (HIV) infection.

Presence of any medical condition or disability that, in the investigator's opinion, could interfere with the assessment of safety or efficacy in this trial or compromise the safety of the subject, including clinically significant ECG abnormalities during the Screening Visit, the Baseline Visit, or Treatment Visit.

Currently pregnant or breastfeeding female subject, or male subject with a pregnant or breastfeeding partner.

Females of childbearing potential who are unable or unwilling to practice highly effective contraception (pregnancy prevention).

Patients were free to withdraw from the study at any time without giving a reason. The investigator could also withdraw patients from the trial if they deemed it appropriate for safety or ethical reasons or if it was considered to be to be detrimental to the well-being of the patient. The study protocol specified that subjects had to be discontinued from study if the following events occurred between recruitment and drug administrations:

A female subject becomes pregnant.

A subject decides to discontinue the study, or a subject decides to withdraw consent from the study.

Any medical condition that may jeopardize the subject's safety if the study drug is administered, in the investigator's opinion.

Discontinuation is deemed to be in the best interest of the subject, in the investigator's opinion.

Ultimately, no patient withdrew from the study, and consequently, no EWV were performed.

A total of 16 patients were screened. A total of 12 patients received the treatment and completed the study. Efficacy and safety data were analysed for the 12 patients. A sample size of 10-15 patients was considered sufficient to estimate the antitussive effect of a single dose of therapy, in terms of magnitude and duration, as compared with the baseline measurement.

Treatment

Subjects took a single orally disintegrating tablet (ODT) with 5 mg AX-8 in the morning on the first day of the treatment period (Day 1). This Investigational Medical Product (IMP) was let to dissolve on the tongue. Patients were observed for 5 minutes to ensure that the tablet was dissolved on the tongue and not swallowed.

The ODT was administered on Day 1 (Visit 3; Treatment Visit) after the cough monitor from Day 0 (Visit 2, Baseline Visit) had been removed and before 10 am (because patients with RCC primarily cough during the daytime).

The AX-8 ODTs also contain Ludiflash® (Mannitol, Kollidon® CL-SF, Kollicoat® SR 30D), sorbitol, silica colloidal anhydrous, and magnesium stearate. The IMP batch was number 17081402 (expiry date November 2018). The ODTs were kept in the original packaging (i.e., HDPE bottle with polypropylene twist-off cap contained 50 tablets) until administration. The ODT's were stored in a secure, temperature-controlled (not above 30° C.), controlled access location at the study site.

The 5 mg AX-8 dose was selected for this study based on the favourable safety and tolerability profile of AX-8 at the 5 mg ODT dose level, as demonstrated in the Phase 1 study in healthy volunteers. In that study, AX-8 was well tolerated in the 12 subjects exposed to a single dose of AX-8 and there were no remarkable adverse events (AEs).

All study treatment was administered by the study investigator or designated member of staff. To ensure drug accountability, the investigator or designated deputy maintained accurate records of the dates and amounts of drug received, to whom it was dispensed and accounts of any supplies which were accidentally or deliberately destroyed; these details were recorded on a drug accountability form. All unused clinical supplies and the drug accountability forms were returned at the end of the study.

Prior and Concomitant Therapy

Concomitant therapies included any therapies (including over-the-counter (OTC) medications) used by a subject from initiation of treatment through the follow-up period. A record of all medications used was maintained for each subject throughout the study. Reported information included a description of the type of drug, treatment period, dosing regimen, the route of administration, and drug indication.

Subjects using oral contraceptives, hormone-replacement therapy, or other maintenance therapies that were not excluded therapies could continue their use during the study. A record of all concomitant therapies was maintained for each subject.

The following therapies and products were excluded within the last 6 hours prior to and during all visit days:
 Consumption of cough sweets, over the counter cough syrups, chewing gum, caffeine, chili or products containing mint and/or menthol within the last 6 hours prior to and during visit days.

The following therapies were excluded from 1 week prior to the Baseline Visit (Day 0, Visit 2) until the end of the Follow-Up Visit (Day 2, Visit 4):

Opioids (including codeine and morphine). Opioids (including codeine), if required for other indications, were permitted provided that subjects were receiving a stable dose for at least one week prior to the Baseline Visit (Day 0) and still experiencing a troublesome cough. Subjects had to remain on a stable dose for the duration of the treatment period.

The following cough therapies were excluded from 2 weeks prior to the Baseline Visit (Day 0, Visit 2) until the End of Study Visit (Visit 5):
 Dextromethorphan;
 Guaifenesin.

The following therapies were excluded from 2 weeks prior to the Baseline Visit (Day 0, Visit 2) until the End of Study Visit (Visit 5):
 Pregabalin, gabapentin, thalidomide, or amitriptyline for the treatment of cough. Pregabalin, gabapentin, thalidomide, or amitriptyline if required for other indications, were permitted if subjects were receiving a stable dose and still experiencing a troublesome cough. Subjects had to remain on a stable dose for the duration of the treatment period.

The following therapies were excluded from 4 weeks prior to the Baseline Visit (Day 0, Visit 2) until the End of Study Visit (Visit 5):
 Systemic immunosuppressive/immunomodulatory therapies (including but not limited to PDE4 inhibitors, cyclosporine, mycophenolate-mofetil, methotrexate, azathioprine, or phototherapy);
 Any investigational therapy.

The following therapies were excluded from 8 weeks prior to the Baseline Visit (Day 0, Visit 2) until the End of Study Visit (Visit 5):
 Biologic therapies;
 Investigational biologic therapies.

The following therapy was excluded from 12 weeks prior to the Baseline Visit (Day 0, Visit 2) until the End of Study Visit (Visit 5):
 Treatment with an ACE-inhibitor.

Subjects were asked to take appropriate measures to minimize exposure to UV-radiation (e.g., sunlight, tanning booths) from the Treatment Visit (Day 1, Visit 3) through to the End of Study Visit (Visit 5).

Assessment of Efficacy

Objective Cough Frequency:

Objective cough frequency was measured as 24-hour sound recordings using a custom-built digital recording device (VitaloJAK, Vitalograph, Ltd).

VitaloJAK™ is a semi-automated 24-hour ambulatory cough monitoring system (Vitalograph; Buckinghamshire, England) operating in a manner which completely replicates routine practice. The 24-hour recordings are compressed using custom designed compression software, using an algorithm. The VitaloJAK™ is a reliable, robust and efficient tool for the objective measurement of cough frequency. Importantly it reduces 24-hour recordings by up to 98% whilst preserving close to 100% of recorded cough sounds. It is worn like a Holter monitor, with a single sensor affixed to the patient's chest wall. An optional second channel via a conventional microphone (worn, for example, on the patient's shirt) allows quality assurance with human intervention. The device itself is attached on the trousers, skirt, etc.

Cough Severity:

Cough Severity was scored on a 100 mm Visual Analog Scale (VAS) at the specified time points. The patient was asked to indicate their assessment by marking (e.g., with a pen) a position along a 100 mm line between two extremes, e.g., "no cough" and "worst cough".

Urge-to-Cough (UTC):
Urge-to-cough was scored on a 100 mm VAS at the specified time points.

Throat Irritation:
Throat irritation was scored on a 100 mm VAS at the specified time points.

Throat Cooling:
Throat cooling was scored on a 100 mm VAS at the specified time points.

Global Rating of Change Scale (GRCS):
The GRCS was used by subjects to assess their overall status for the specified periods (the 4-hour period following dose; and the 24-hour period following dose). It consisted of a 14-point scale ranging from 'a very great deal better' to 'a very great deal worse'.

Taste Questionnaire:
A simple taste observation (qualitative) was completed. Freshness, basic tastes (i.e., sweet, sour, bitter, and salty), and palatability were scored on 100 mm VAS's at the specified time points.

Assessment of Safety
Safety assessments consisted of monitoring and recording protocol-defined adverse events (AEs) and serious adverse events (SAEs); vital signs; physical examinations; clinical laboratory assessments; electrocardiograms (ECGs); and other protocol-specified tests that were deemed critical to the safety evaluation of the study drug.

Vital signs included measurements of heart rate, sitting blood pressure, respiration rate, and temperature. Vital signs were assessed at the specified time points and at unscheduled study visits when clinically indicated. The subjects' height and weight were also measured.

Physical examinations were performed at the specified time points and at unscheduled study visits when clinically indicated, covering major body systems (assessment of the ears, eyes, nose and throat, head, neck, thyroid, neurological system, respiratory system, cardiovascular system, lymph nodes, abdomen, skin, musculoskeletal, neurological).

Samples for hematology, chemistry, urinalysis, and serum pregnancy testing (when necessary) were collected at the specified time points and at unscheduled study visits when clinically indicated and analysed at a local laboratory unless otherwise specified.

Laboratory assessments included the following:
Hematology: haematocrit, hemoglobin, red blood cell count, red blood cell indices, platelets, white blood cell count, white blood cell differential (neutrophils, lymphocytes, monocytes, basophils, eosinophils).
Chemistry: sodium, potassium, chloride, bicarbonate, glucose, blood urea nitrogen, creatinine, eGFR, calcium, phosphorus, magnesium, albumin, ALT, AST, alkaline phosphatase, total bilirubin, LDH, uric acid, total protein, lipid panel.
Pregnancy testing: all females of childbearing potential had a local urine pregnancy test performed. Positive or equivocal urine pregnancy test results were confirmed by a serum pregnancy test analysed at a local laboratory. A serum pregnancy test was done at in the Screening Visit (Visit 1).
Urinalysis: pH, specific gravity, bilirubin, glucose, ketones, leukocytes, nitrite, blood, protein, urobilinogen, microscopic analysis.

A standard 12-lead ECG was performed at the specified time points and at unscheduled study visits when clinically indicated.

Lung function tests (FEV1, FVC and FEV1/FVC ratio) was assessed using a spirometer:
Forced expiratory volume in one second (FEV1) is the amount of air exhaled within one second using the spirometer.
Forced vital capacity (FVC) is the total amount of air that can be exhaled in one breath.
FEV1 divided by FVC (FEV1/FVC) this is the proportion of the total that can be exhaled in one second.

Schedule of Activities and Assessments
Informed consent was obtained prior to any protocol-mandated procedures, including the stopping of any excluded therapies.

Screening Visit (Visit 1):
Screening assessments were conducted over a 14-day period prior to the Baseline Visit. The Screening Period could have been extended beyond 14 days if any additional follow-up on findings from any of the Screening assessments was required.

The following screening procedures were performed (not specified by the order below):
Inclusion/exclusion criteria review.
Demographics and Medical history (including chronic cough history, history of any medications within 30 days prior to Screening Visit and chronic cough treatments within 1 year prior to Screening Visit).
Physical examination.
Vital signs (including height and weight).
12-Lead ECG.
Spirometry.
Chest radiograph or CT Thorax (if not done within the past 5 years).
Laboratory tests:
    Serum pregnancy test for females of childbearing potential.
    Hematology.
    Chemistry.
    Urinalysis.
    Urine drug screen.
Cough severity VAS assessment.
Urge-to-cough VAS assessment.
Throat irritation VAS assessment.
Schedule Baseline Visit.

Baseline Visit (Visit 2; Day 0):
At the Baseline visit, the following procedures and assessments were performed (not specified by the order below):
Inclusion/exclusion criteria review.
Update medical history.
Record all concomitant medication use.
Vital signs.
12-Lead ECG.
Laboratory tests:
    Urine pregnancy test for females of childbearing potential.
    Urine drug screen.
Provide subject with VAS diary and instruct them to complete VAS assessments at +5 and +6 hours at home (see below).
Attach and activate the Baseline Visit cough monitor (preferably before 10 am).
Cough severity VAS assessment:
    Prior to cough monitor installation:
        −30 minutes.
    After cough monitor installation:
        +1, +2, +3, +4, +5, +6 hours.

Urge-to-cough VAS assessment:
  Prior to cough monitor installation:
    −30 minutes.
  After cough monitor installation:
    +1, +2, +3, +4, +5, +6 hours.
Throat irritancy VAS assessment:
  Prior to cough monitor installation:
    −30 minutes.
  After cough monitor installation:
    +1, +2, +3, +4, +5, +6 hours.
Schedule Treatment Visit.

The VAS assessments at +5 and +6 hours were completed at home by the patient using a VAS diary. VAS assessments at all other time points were completed in the unit. A time window of +/−5 minutes was permitted at all VAS time points.

Treatment Visit (Visit 3; Day 1):

At least 24 hours after the Baseline Visit cough monitor has been attached on Day 0, and preferably before 10 am, the following activities were performed by clinic staff (not specified by the order below):
  Remove the Baseline Visit cough monitor.
  Update medical history.
  Record all concomitant medication use.
  Inclusion/exclusion criteria review.
  If all inclusion and exclusion criteria were met, enroll patient into study.
  Vital signs: before dose and 4 hours after dose.
  12-lead ECG (before dose).
  Laboratory tests:
    Urine drugs-of-abuse testing.
  Pharmacokinetic (PK) sample taken.
  Provide subject with VAS diary and instruct them to complete VAS assessments at +5 and +6 hours at home (see below).
  Before dosing, attach and activate Treatment Visit cough monitor.
  Administer the dose of the study drug (preferably before 10 am).
  Cough severity VAS assessment:
    Prior to dose:
      −30 minutes.
    After dose:
      +1, +2, +3, +4, +5, +6 hours.
  Urge-to-cough VAS assessment:
    Prior to dose:
      −30 minutes.
    After dose:
      +1, +2, +3, +4, +5, +6 hours.
  Throat irritancy VAS assessment:
    Prior to dose:
      −30 minutes.
    After dose:
      +1, +2, +3, +4, +5, +6 hours.
  Throat cooling VAS assessment:
    Prior to dose:
      −30 minutes.
    After dose:
      +1, +2, +3, +4, +5, +6 hours.
  GRCS assessment at 4 hours after dose.
  Schedule Follow-Up Visit.
  Once the Investigator confirmed it was safe to do so, the subject could leave the unit after the assessments 4 hours after dose were complete.

The VAS assessments at +5 and +6 hours were completed at home by the patient using a VAS diary. VAS assessments at all other time points were completed in the unit. A time window of +/−5 minutes was permitted at all VAS time points.

Follow-Up Visit (Visit 4; Day 2):

At least 24 hours after the Treatment Visit cough monitor has been attached (on Day 1), the following activities were performed by clinic staff (not specified by the order below):
  Remove the Treatment Visit cough monitor.
  Collect and review the VAS diary for completeness.
  Overall impression of the treatment day (24 hours) with:
    Cough severity VAS assessment.
    Urge-to-cough VAS assessment.
    Throat irritancy VAS assessment.
    Throat cooling VAS assessment.
  GRCS assessment.
  Record all adverse events.
  Record all concomitant medication use.
  Schedule End of Study visit.

End of Study Visit (Visit 5):

The following procedures and evaluations were performed at the clinic between Day 7 and 14. At this visit, the following procedures and assessments were performed by clinic staff (not specified by the order below):
  Cough severity VAS assessment.
  Urge-to-cough VAS assessment.
  Throat irritancy VAS assessment.
  GRCS assessment.
  Vital signs.
  Weight.
  Physical examination.
  12-lead ECG.
  Laboratory tests:
    Hematology.
    Chemistry.
    Urinalysis.
    Urine pregnancy test for females of childbearing potential.
  Record all adverse events.
  Record all concomitant medication use.

The following table summarises the timing of the various procedures and evaluations.

TABLE 4

Schedule of Procedures and Evaluations

| Study Period Study Visit | Screening Visit 1 Screening Visit | Baseline Visit 2 Baseline Visit | Visit 3 Treatment Visit | Treatment Visit 4 Follow-up Visit | End of Study Visit 5 End of Study Visit |
|---|---|---|---|---|---|
| Study Schedule | Day−14 to Day−1 [a, b] | Day 0 [n] | Day 1 [o] | Day 2 | Day 7–14 |

TABLE 4-continued

Schedule of Procedures and Evaluations

| Study Period<br>Study Visit | Screening<br>Visit 1<br>Screening<br>Visit | Baseline<br>Visit 2<br>Baseline<br>Visit | Visit 3<br>Treatment<br>Visit | Treatment<br>Visit 4<br>Follow-<br>up<br>Visit | End of<br>Study<br>Visit 5<br>End of<br>Study<br>Visit |
|---|---|---|---|---|---|
| Study Procedure | — | — | — | — | — |
| Written Informed Consent[g] | X [g] | | | | |
| Inclusion/Exclusion Criteria | X | X | X | | |
| Demographics; Medical & Medication History | X | X | | | |
| Chest Radiograph or CT Thorax[e] | X [e] | | | | |
| Physical Examination | X | | | | X |
| Vital Signs | X | X | X [l] | | X |
| Height & Weight | X | | | | X [f] |
| ECG (12-lead) | X | X | X [l] | | X |
| Spirometry | X | | | | |
| Clinical Laboratory Sampling | X | | | | X |
| Urinalysis | X | | | | X |
| Urine Drug Screen | X | X | X | | |
| Serum Pregnancy Test | X | | | | |
| Urine Pregnancy Test | | X | | | X |
| PK Sample | | | X [k] | | |
| Attach Cough Monitor | | X [d] | X [c,d] | | |
| Remove cough monitor | | | X [c] | X | |
| Adverse Event Monitoring | | | X | X | X |
| Concomitant Medications | X | X | X | X | X |
| Cough Severity VAS Assessment | X | X [h] | X [h] | X [j] | X |
| Urge-to-Cough VAS Assessment | X | X [h] | X [h] | X [j] | X |
| Throat Irritation VAS Assessment | X | X [h] | X [h] | X [j] | X |
| Throat Cooling VAS Assessment | | | X [i] | X [j] | |
| Study Drug Administration | | | X [c] | | |
| Issue VAS diary for subjects to take home | | | X [h,i] | | |
| Collect and review VAS diary | | | | X | |
| GRCS Assessment | | | X | X | X |
| Taste Questionnaire | | X [h] | X [m] | X [j] | |

Notes:

[a] Multiple clinic visits could be required to complete all screening assessments.

[b] The Screening Period could have been extended beyond 14 days if any additional follow-up on findings from any of the Screening assessments was required.

[c] Single dose of study drug (an orally disintegrating tablet (ODT) having 5 mg AX-8, administered orally and dissolved on the tongue) administered on Day 1 after the Baseline Visit cough monitor had been removed and preferably before 10 am. The Treatment Visit cough monitor was attached and started before dosing.

[d] Cough monitor was attached, preferably before 10 am, and worn for 24 hours during each assessment.

[e] If not done within the past 5 years.

[f] Weight only.

[g] Informed consent had to be obtained prior to any protocol-mandated procedures, including stopping of any excluded therapies.

[h] Performed at the following time points:
- On Day 0: prior to cough monitor installation: −30 minutes; after cough monitor installation: +1, +2, +3, +4, +5, +6 hours.
- On Day 1: prior to dosing: −30 minutes; after doing: +1, +2, +3, +4, +5, +6 hours.
- The VAS assessments at +5 and +6 hours were completed at home by the patient using a VAS diary. VAS assessments at all other time points were completed in the unit. A time window of +/− 5 minutes was permitted at all VAS time points.

[i] Performed at the following time points:
- On Day 1: prior to dosing: -30 minutes; after doing: +1, +2, +3, +4, +5, +6 hours.
- The VAS assessments at +5 and +6 hours were completed at home by the patient using a VAS diary. VAS assessments at all other time points were completed in the unit. A time window of +/− 5 minutes was permitted at all VAS time points.

[j] VAS or Taste Questionnaire for last 24 hours, overall impression of the treatment day.

[k] A pharmacokinetic (PK) sample was taken any time before dosing on Day 1, and then after dosing: +15 minutes, +30 minutes, +45 minutes, +1 hour, +1.25 hours, +1.50 hours, +1.75 hours, +2 hours, +2.5 hours, +3 hours, +3.5 hours, and +4 hours.

[l] 12-Lead ECG and vital sign assessments were performed any time before dose and 4 hours after dose.

[m] Taste Questionnaire was completed 15 minutes before dosing, after dosing: +3 to 10 minutes, +2 hours.

[n] Day 0: (Baseline Visit) Patient stayed for a minimum of 4 h at the clinic after installation of cough monitor, in total 4-5 hours.

[o] Day 1: (Treatment Visit) Patient stayed for a minimum of 4 hours after dosing at the clinic, in total 5-6 hours.

Endpoints

The primary efficacy endpoint was the change from baseline in awake objective cough frequency over 24 hours after 1 dose of treatment.

The key secondary efficacy endpoints were:
Change from Baseline in hourly objective cough frequency over a 24-hour monitoring period.
Proportion of subjects with ≥30% reduction in 24-hour cough frequency per hour.
Proportion of subjects with ≥30% reduction in awake cough frequency per hour.
Change from Baseline in cough severity VAS.
Change from Baseline in urge-to-cough VAS.
Change from Baseline throat irritation.
Throat cooling VAS.
Global Rating of Change Scale (GRCS).

Efficacy Variables

The 24-hour cough frequency (coughs per hour) for a specified visit was calculated as: 24-hour cough frequency=(total number of cough events during the monitoring period (24-hour interval))/24.

The awake cough frequency (coughs per hour) is defined as below:

Awake cough frequency=(total number of cough events during the monitoring period (24-hour interval) while the subject was awake)/(total duration (in hours) during the monitoring period (24-hour interval) that the subject was awake).

Awake duration (hours) was defined as the time between waking up and sleeping during the 24-hour monitoring period.

The cough data contains all cough events that occurred during that 24-hour monitoring period as well as the information about "asleep time" and "awake time". Any session with duration of recording <4 hours was considered as missing.

In general, each 24-hour session was composed of an awake monitoring period and an asleep monitoring period. If a subject did not wake up before the end of the recording session, it was assumed that the subject slept for the rest of the session. The session will then have missing awake time, and the rest of session will be considered under the asleep monitoring period. For any session with both asleep time and awake time missing, the entire 24-hour session was considered under the awake monitoring period, unless the session had early termination of recording.

On each collection day, the cough count, the actual cough monitoring duration (in hours), and the coughs per hour were derived for the total 24-hour period, the awake period, and the asleep period, respectively.

The percent change in awake coughs per hour is defined as below:

Percent change in awake cough frequency=[(Change from baseline in awake cough frequency×100)/(Baseline awake cough frequency)].

The proportion of participants with ≥30% of reduction from baseline in awake cough frequency is the number of participants with ≤−30% change in awake cough frequency divided by the total number of participants with available data.

Where the geometric mean (95% confidence interval (CI)) of 24-hour cough frequency was presented, any observation of zero cough per hour was replaced by a cough rate of 0.1/hour for the calculation of the geometric mean.

Patient Participation

Sixteen patients were screened between 12 Dec. 2017 and 16 May 2018 and 11 patients completed end of study visits between 8 Jan. 2018 and 11 Jun. 2018.

Patient participation is summarised in the following tables.

TABLE 5A

Individual Patient Visits

| Subject # | Screening Visit (Visit 1) Date (mm/dd/yyyy) | Status | Baseline Visit (Visit 2) Date (mm/dd/yyyy) | Status | Treatment Visit (Visit 3) Date (mm/dd/yyyy) | Status |
|---|---|---|---|---|---|---|
| 1 | 12/12/2017 | drop-out | n.a. | n.a. | n.a. | n.a. |
| 2 | 12/18/2017 | accepted | 12/20/2017 | done | 12/21/2017 | done |
| 3 | 12/21/2017 | accepted | 01/03/2018 | done | 01/04/2018 | done |
| 4 | 01/02/2018 | accepted | 01/08/2018 | done | 01/09/2018 | done |
| 5 | 01/03/2018 | accepted | 01/15/2018 | done | 01/16/2018 | done |
| 6 | 01/08/2018 | accepted | 01/16/2018 | done | 01/17/2018 | done |
| 7 | 01/08/2018 | accepted | 01/17/2018 | done | 01/18/2018 | done |
| 8 | 01/15/2018 | drop-out | n.a. | n.a. | n.a. | n.a. |
| 9 | 01/22/2018 | accepted | 01/30/2018 | done | 01/31/2018 | done |
| 10 | 02/28/2018 | accepted | 03/07/2018 | done | 03/08/2018 | done |
| 11 | 03/13/2018 | accepted | 03/19/2018 | done | 03/20/2018 | done |
| 12 | 03/19/2018 | drop-out | n.a. | n.a. | n.a. | n.a. |
| 13 | 04/30/2018 | accepted | 05/08/2018 | done | 05/09/2018 | done |
| 14 | 05/01/2018 | accepted | 05/09/2018 | done | 05/10/2018 | done |
| 15 | 05/09/2018 | drop-out | n.a. | n.a. | n.a. | n.a. |
| 16 | 05/16/2018 | accepted | 05/29/2018 | done | 5/30/2018 | done |

TABLE 5B

Individual Patient Visits

| Subject # | Follow-Up Visit (Visit 4) Date (mm/dd/yyyy) | Status | End of Study Visit (Visit 5) Date (mm/dd/yyyy) | Status | Comments |
|---|---|---|---|---|---|
| 1 | n.a. | n.a. | n.a. | n.a. | Screen fail |
| 2 | 12/22/2017 | done | 01/04/2018 | done | |
| 3 | 01/05/2018 | done | 01/12/2018 | done | |
| 4 | 01/10/2018 | done | 01/22/2018 | done | |
| 5 | 01/17/2018 | n.a. | 01/24/2018 | done | Did not attend |
| 6 | 01/18/2018 | done | 01/24/2018 | done | |
| 7 | 01/19/2018 | done | 01/29/2018 | n.a. | |
| 8 | n.a. | n.a. | n.a. | n.a. | Screen fail |
| 9 | 02/01/2018 | done | 02/08/2018 | done | |
| 10 | 03/09/2018 | done | 03/16/2018 | done | |
| 11 | 03/21/2018 | done | 03/28/2018 | done | |
| 12 | n.a. | n.a. | n.a. | n.a. | Screen fail |
| 13 | 05/10/2018 | done | 05/16/2018 | done | |
| 14 | 05/11/2018 | done | 05/23/2018 | done | |
| 15 | n.a. | n.a. | n.a. | n.a. | Screen fail |
| 16 | 05/31/2018 | done | 06/11/2018 | done | |

Patient Demographics

The demographics of the 12 patients are summarised in the following table.

TABLE 6

Patient Demographics

| Gender | n | 12 |
|---|---|---|
| | Male | 3 |
| | Female | 9 |
| Age (years) | n | 12 |
| | Mean | 63.9 |
| | Min | 50 |
| | Max | 78 |
| Ethnicity | n | 12 |
| | White | 12 |
| Height (m) | n | 12 |
| | Mean | 1.63 |
| | Min | 1.50 |
| | Max | 1.84 |
| Weight (kg) | n | 12 |
| | Mean | 67.5 |
| | Min | 42.2 |
| | Max | 108.0 |
| BMI (kg/m$^2$) | n | 12 |
| | Mean | 25.0 |
| | Min | 18.8 |
| | Max | 32.3 |
| FEV1 % predicted | n | 12 |
| | Mean | 97.5 |
| | Min | 69.0 |
| | Max | 133.0 |
| FVC % predicted | n | 12 |
| | Mean | 111.6 |
| | Min | 79.0 |
| | Max | 152.0 |
| Duration Chronic Cough (years) | n | 8 (*) |
| | Median | 12.5 |
| | Min | 2.6 |
| | Max | 40 |

(*) No data available for 4 of the 12 patients

Results—Cough Frequency

The raw hourly cough count data relative to dosing time was plotted for the full analysis set and inspected as an initial step.

FIG. 1 is a graph of median cough frequency (coughs/hour) versus time after treatment (hours) for baseline (open circles) and treatment (filled circles).

The data suggest that treatment with a single dose of 5 mg AX-8 resulted in improvement in the hourly cough frequency as compared to baseline over a period of approximately 8 hours.

Summary cough frequency data for each of the five time windows (24 hours; awake; asleep; 8 hours; 4 hours) are shown in the following table.

TABLE 7

Cough Frequency Data for Various Time Windows

| Time Window | Variable | Baseline (coughs/hour) | Treatment (coughs/hour) | Change |
|---|---|---|---|---|
| 24 hours | n | 12 | 12 | |
| | Median | 48.1 | 44.3 | −7.90% |
| | Min | 10.7 | 1.6 | |
| | Max | 83.8 | 185.7 | |
| Awake | n | 12 | 12 | |
| | Median | 64.1 | 54.8 | −14.5% |
| | Min | 15.2 | 2.4 | |
| | Max | 107.0 | 232.8 | |
| Asleep | n | 12 | 12 | |
| | Median | 7.1 | 3.7 | −47.9% |
| | Min | 0.6 | 0.0 | |
| | Max | 49.5 | 92.8 | |
| 8 hours | n | 12 | 12 | |
| | Median | 75.5 | 45.4 | −39.9% |
| | Min | 13.3 | 1.2 | |
| | Max | 107.1 | 203.5 | |
| 4 hours | n | 12 | 12 | |
| | Median | 71.0 | 53.4 | −24.8% |
| | Min | 13.5 | 0.5 | |
| | Max | 123.3 | 202.0 | |

For awake and asleep cough frequencies, baseline and treatment data were compared using Wilcoxon signed rank test due to the skewed nature of the data. The data are summarised in the following table.

TABLE 8

Cough Frequency (Coughs/Hour) for Awake and Asleep Time Windows (Wilcoxon signed-rank test)

| Awake | Baseline | n | 12 |
|---|---|---|---|
| | | Median (IQR) | 64.1 (27.4-94.4) |
| | Treatment | n | 12 |
| | | Median (IQR) | 54.8 (16.4-79.5) |
| | | p-value | 0.034 |

TABLE 8-continued

Cough Frequency (Coughs/Hour) for Awake and Asleep Time Windows
(Wilcoxon signed-rank test)

| | | | |
|---|---|---|---|
| Asleep | Baseline | n | 12 |
| | | Median (IQR) | 7.1 (1.6-19.8) |
| | Treatment | n | 12 |
| | | Median (IQR) | 3.7 (0.6-17.5) |
| | | p-value | 0.272 |

IQR = Interquartile Range.

These data suggest a significant reduction in cough frequency during waking hours (from 64.1 to 54.8; 14.5% reduction). During sleep, cough frequency is much lower and more variable and therefore although the cough rate is numerically reduced (from 7.1 to 3.7; 48% reduction), the difference may not be statistically significant for the sample size (12 patients) used.

For 24 hour-, 8 hour-, and 4 hour-cough frequencies, baseline and treatment data were compared using General Estimating Equations (GEE) models. Prior to analysis, these cough count data were natural log (Ln) transformed in order to normalise the distribution of the data. As some individual hourly cough counts were zero, 0.1 was added to all values prior to transformation. The data are summarised in the following table.

TABLE 9

Cough Frequency (Coughs/Hour) for 24, 8, and 4 Hour Time Windows
(General Estimating Equations (GEE) models)

| | | | |
|---|---|---|---|
| 24 hours | Baseline | n | 12 |
| | | Ln Mean (SE) | 2.87 (0.19) |
| | Treatment | n | 12 |
| | | Ln Mean (SE) | 2.70 (0.33) |
| | | Treatment ratio | −0.166 |
| | | 95% Cl | −0.53 to 0.20 |
| | | Percentage Change* | −15.3% |
| | | p-value | 0.368 |
| 8 hours | Baseline | n | 12 |
| | | Ln Mean (SE) | 3.72 (0.22) |
| | Treatment | n | 1224 |
| | | Ln Mean (SE) | 3.26 (0.39) |
| | | Treatment ratio (95% Cl) | −0.461 (−0.88 to −0.04) |
| | | Percentage Change* | −36.9% |
| | | p-value | 0.033 |
| 4 hours | Baseline | n | 12 |
| | | Ln Mean (SE) | 3.92 (0.19) |
| | Treatment | n | 12 |
| | | Ln Mean (SE) | 3.38 (0.39) |
| | | Treatment ratio (95% Cl) | −0.54 (−1.08 to −0.01) |

TABLE 9-continued

Cough Frequency (Coughs/Hour) for 24, 8, and 4 Hour Time Windows
(General Estimating Equations (GEE) models)

| | |
|---|---|
| Percentage Change* | −42.0% |
| p-value | 0.047 |

SE = Standard Error. Cl = Confidence Interval.

These data suggest that hourly cough frequency was significantly improved for treatment as compared to baseline over both the 4-hour period and the 8-hour period. It appears that the effect may diminish after 8 hours, and so, when analysed over the full 24-hour recording period, cough frequency is not significantly reduced.

Data for individual subjects for each of the five time windows (awake; asleep; 24 hours; 8 hours; 4 hours) are shown in FIGS. 2-6.

Figure 2:
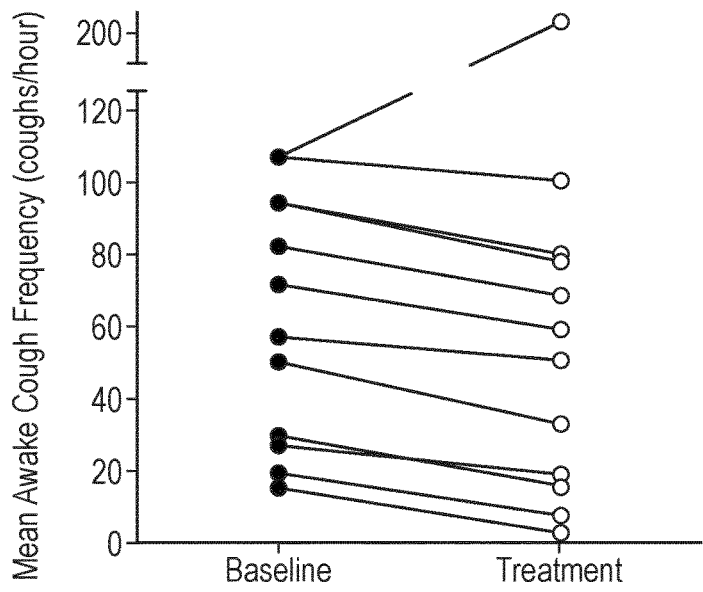
FIG. 2 is a graph showing mean awake cough frequency (coughs/hour) for the 12 individual patients, for both baseline and treatment.

FIG. 2 is a graph showing mean awake cough frequency (coughs/hour) for the 12 individual patients, for both baseline and treatment.

Figures 3, 4:
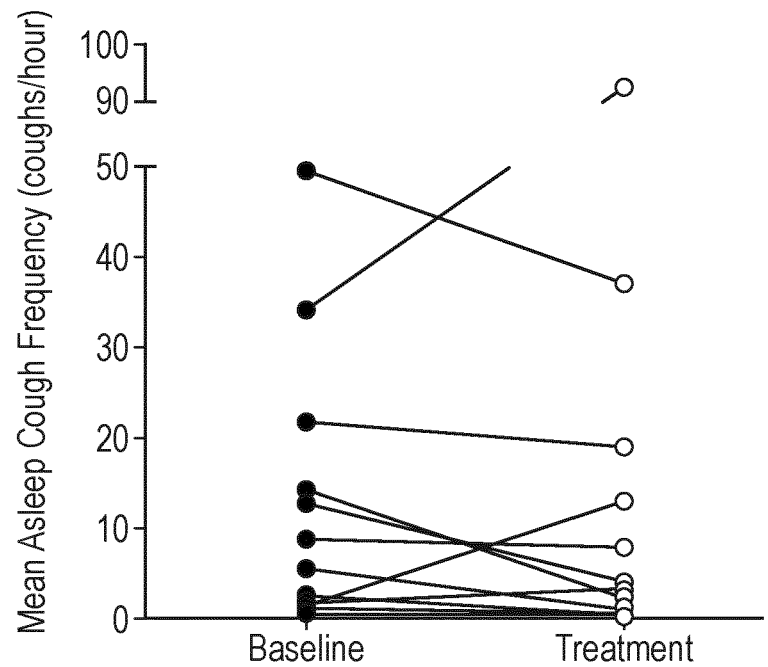
FIG. 3 is a graph showing mean asleep cough frequency (coughs/hour) for the 12 individual patients, for both baseline and treatment.
FIG. 4 is a graph showing mean cough frequency (coughs/hour) for the 12 individual patients during the 24-hour period after treatment and the equivalent baseline period.

FIG. 3 is a graph showing mean asleep cough frequency (coughs/hour) for the 12 individual patients, for both baseline and treatment.

FIG. 4 is a graph showing mean cough frequency (coughs/hour) for the 12 individual patients during the 24-hour period after treatment and the equivalent baseline period.

(It was subsequently determined that the values reported in FIG. 2, FIG. 3, and FIG. 4 are "mean" values and not "median" values as originally reported.)

Figure 5:
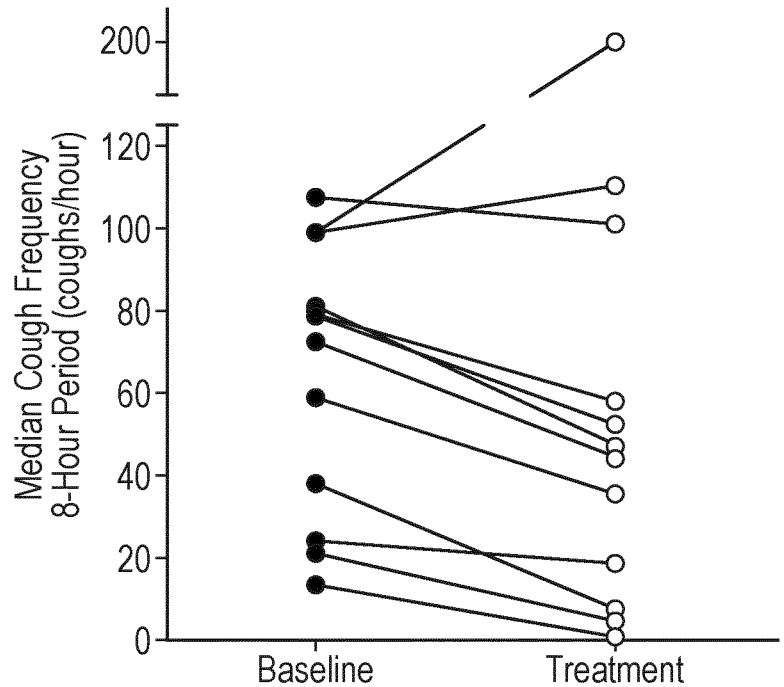
FIG. 5 is a graph showing median cough frequency (coughs/hour) for the 12 individual patients during the 8-hour period after treatment and the equivalent baseline period.

FIG. 5 is a graph showing median cough frequency (coughs/hour) for the 12 individual patients during the 8-hour period after treatment and the equivalent baseline period.

Figure 6:
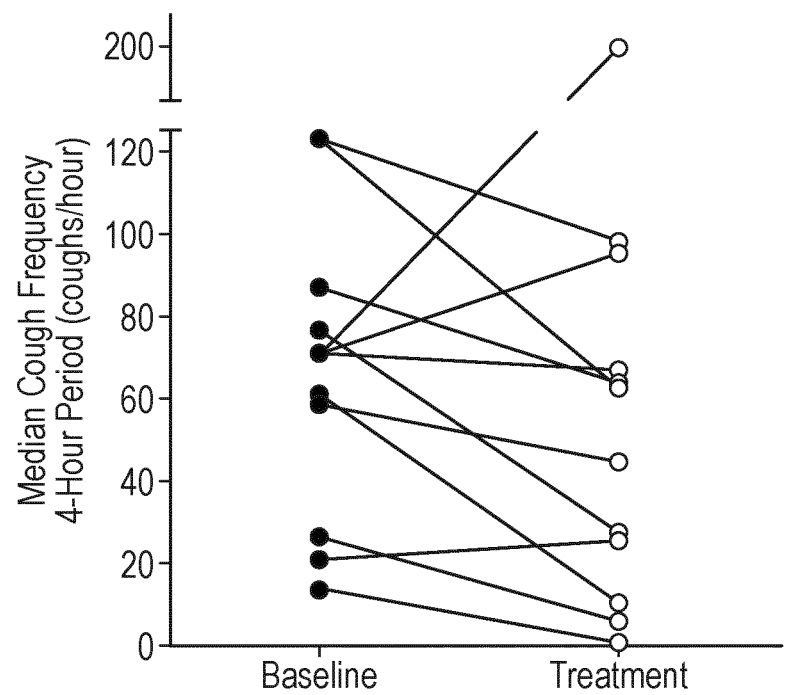
FIG. 6 is a graph showing median cough frequency (coughs/hour) for the 12 individual patients during the 4-hour period after treatment and the equivalent baseline period.

FIG. 6 is a graph showing median cough frequency (coughs/hour) for the 12 individual patients during the 4-hour period after treatment and the equivalent baseline period.

The data demonstrate that:
4/12 subjects (33.3%) experienced a ≥30% reduction in awake cough frequency per hour.
4/12 subjects (33.3%) experienced a ≥30% reduction in 24-hour cough frequency per hour.
5/12 subjects (41.7%) experienced a ≥30% reduction in 4-hour cough frequency per hour.
7/12 subjects (58.3%) experienced a ≥30% reduction in 8-hour cough frequency per hour.

Results—Cough Severity and Associated Sensations

At various time points, patients were asked to report cough severity, throat irritation, urge-to-cough, and throat cooling using 100 mm Visual Analog Scales (VASs).

Data for the Screening Visit and End of Study Visit as well as data for the Follow-Up visit (assessment of the overall ≥24-hour period after dosing) are shown in the following table.

TABLE 10

Cough Severity and Associated Sensations

| | | Screening (Visit 1) | Follow-Up (Visit 4): >24-hour period after treatment | End of Study (Visit 5) |
|---|---|---|---|---|
| Cough Severity | n | 12 | 11 | 11 |
| | Median (a) | 61.5 (62.5) (b) | 47.0 | 64.0 |
| | Min | 46 | 6.0 | 24.0 |
| | Max | 86 | 96.0 | 87.0 |
| Throat Irritation | n | 12 | 11 | 11 |
| | Median (a) | 55.0 (48.7) (b) | 9.0 | 47.0 |
| | Min | 0 | 1.0 | 0.0 |
| | Max | 91 | 97.0 | 87.0 |

TABLE 10-continued

Cough Severity and Associated Sensations

|  |  | Screening (Visit 1) | Follow-Up (Visit 4): >24-hour period after treatment | End of Study (Visit 5) |
|---|---|---|---|---|
| Urge-to-Cough | n | 12 | 11 | 11 |
|  | Median (a) | 51.5 (51.4) (b) | 46.0 | 57.0 |
|  | Min | 1 | 3.0 | 38.0 |
|  | Max | 92 | 95.0 | 85.0 |

(a) It was subsequently determined that these values are "median" values and not "mean" values as originally reported.
(b) It was subsequently determined that the originally reported values (shown in brackets) were incorrectly calculated.

The data show that cough severity decreased substantially following treatment (from 61.5 at Screening, to 47.0 at Follow-Up, and then returning to 64.0 at End of Study). Similarly, the data show that throat irritation decreased substantially following treatment (from 55.0 at Screening, to 9.0 at Follow-Up, and then returning to 47.0 at End of Study). Finally, the data show that urge-to-cough also decreased following treatment (from 51.5 at Screening, to 46.0 at Follow-Up, and then returning to 57.0 at End of Study).

Data for cough severity, throat irritation, urge-to-cough, and throat cooling, both immediately before treatment and hourly for the six hours following treatment, are shown in FIGS. 7-10. (Throat cooling was assessed half-hourly for the first 3 hours following treatment.)

Figure 7:
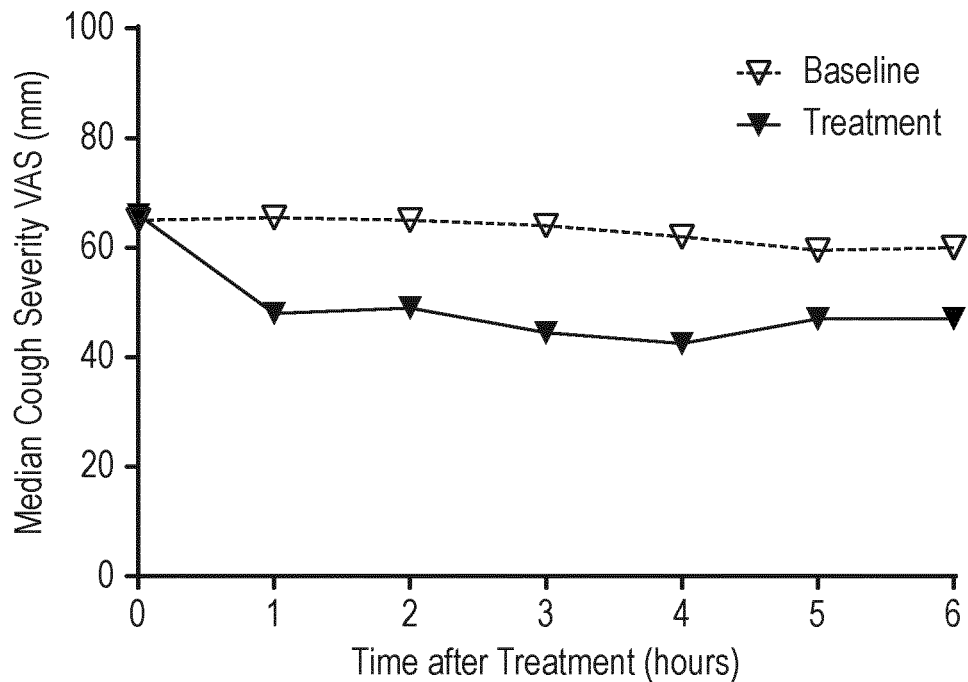
FIG. 7 is a graph of median cough severity (VAS) (mm) versus time after treatment (hours) for baseline (open downward triangles) and treatment (filled downward triangles).

FIG. 7 is a graph of median cough severity (VAS) (mm) versus time after treatment (hours) for baseline (open downward triangles) and treatment (filled downward triangles).

Figure 8:
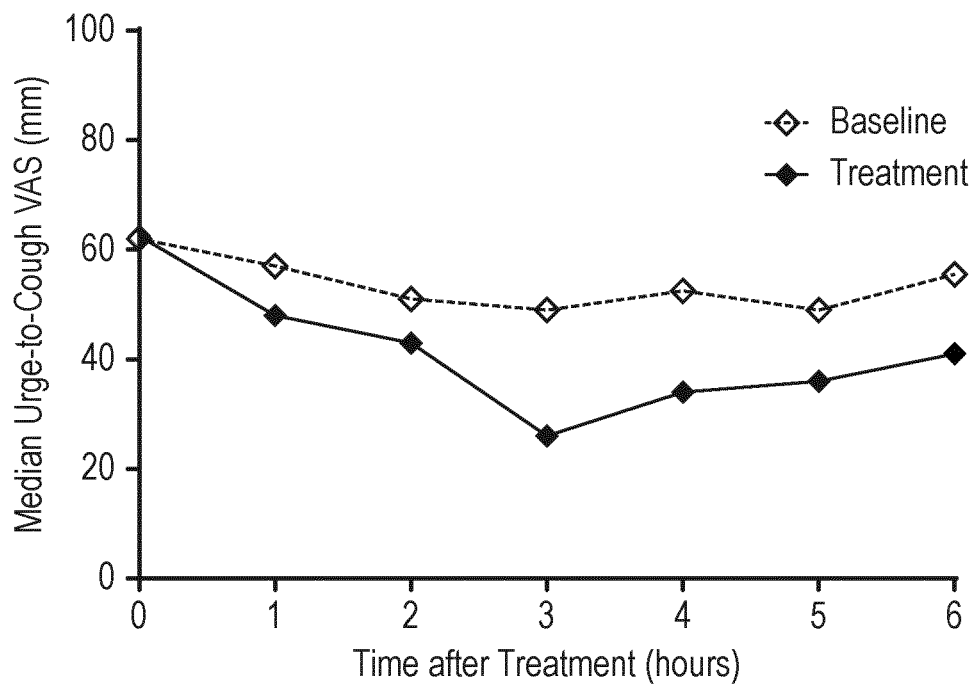
FIG. 8 is a graph of median urge-to-cough (VAS) (mm) versus time after treatment (hours) for baseline (open diamonds) and treatment (filled diamonds).

FIG. 8 is a graph of median urge-to-cough (VAS) (mm) versus time after treatment (hours) for baseline (open diamonds) and treatment (filled diamonds).

Figure 9:
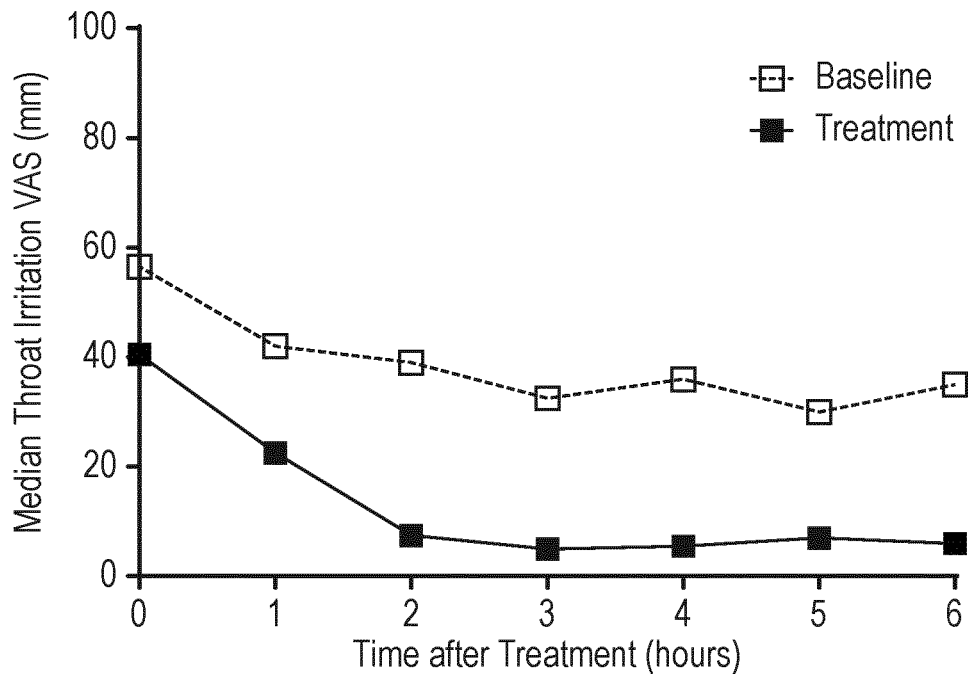
FIG. 9 is a graph of median throat irritation (VAS) (mm) versus time after treatment (hours) for baseline (open squares) and treatment (filled squares).

FIG. 9 is a graph of median throat irritation (VAS) (mm) versus time after treatment (hours) for baseline (open squares) and treatment (filled squares).

Figure 10:
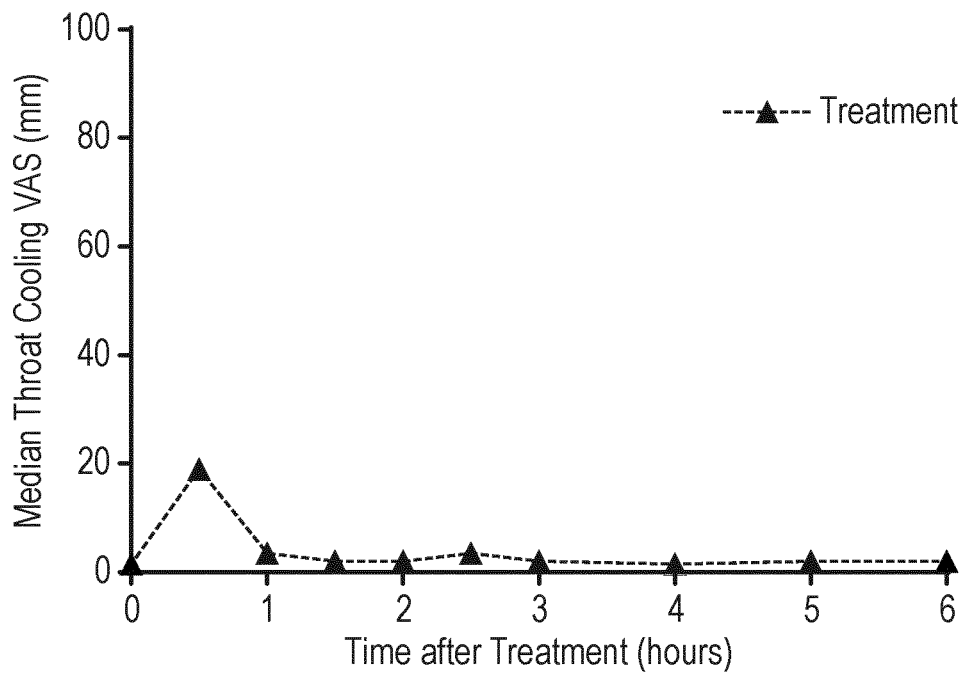
FIG. 10 is a graph of median throat cooling (VAS) (mm) versus time after treatment (hours) (filled upward triangles).

FIG. 10 is a graph of median throat cooling (VAS) (mm) versus time after treatment (hours) (filled upward triangles).

The cough severity data indicates that patients perceived a reduction from the first hour that persisted for the 6 hours of monitoring (see FIG. 7). The urge-to-cough data also indicates an improvement from the first hour that persisted for the 6 hours of monitoring, with an apparent maximum at about 3 hours (see FIG. 8). The throat irritation data also indicates an improvement from the first hour that persisted for the 6 hours of monitoring; however, the baseline is lower on the treatment compared with the baseline day (see FIG. 9). The throat cooling data show an increase only at 30 minutes, and a barely perceptible difference by 1 hour and thereafter (see FIG. 10).

Figure 11:
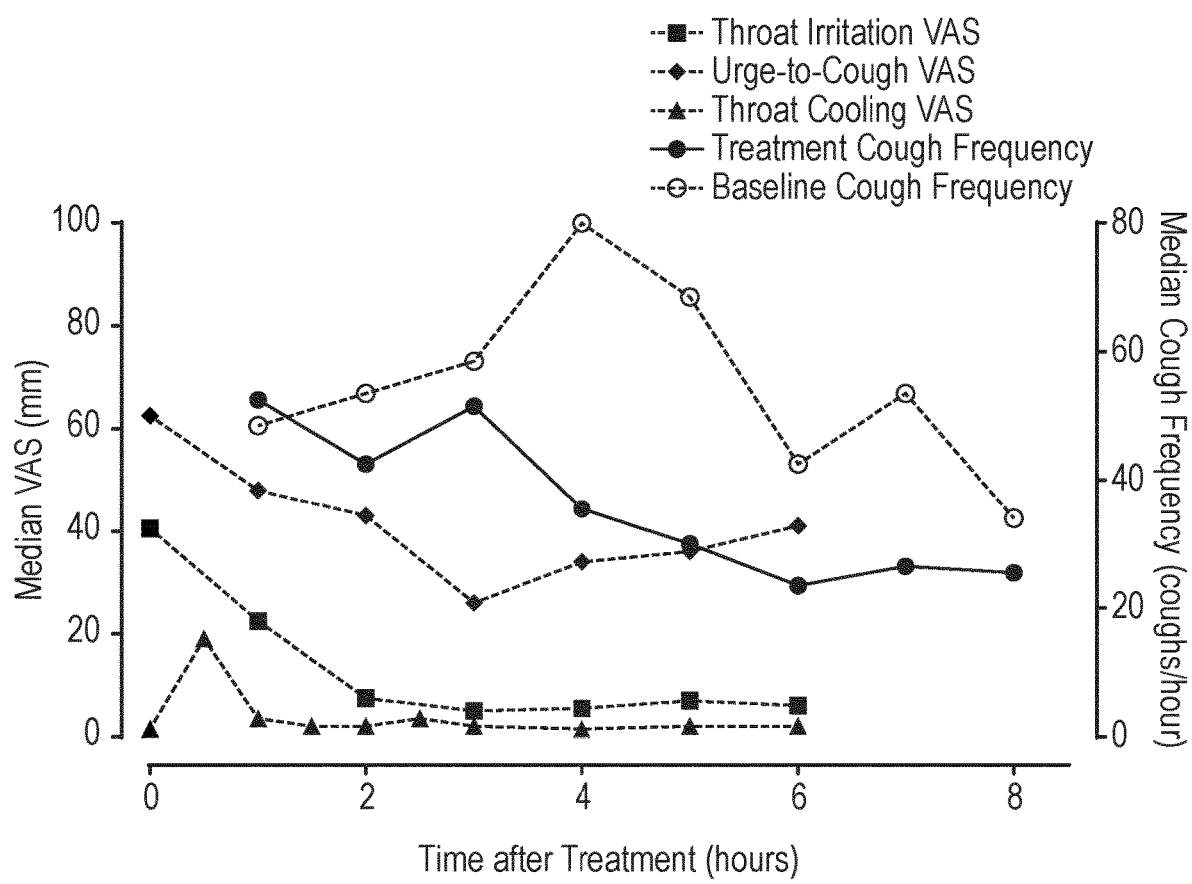
FIG. 11 is a composite graph showing, on the left, median urge-to-cough (VAS) (mm) (filled diamonds), throat irritation (VAS) (mm) (filled squares), and throat cooling (VAS) (mm) (filled upward triangles) and on the right, median cough frequency (coughs/hour) for baseline (open circles) and treatment (filled circles), versus time after treatment (hours).

FIG. 11 is a composite graph showing, on the left, median urge-to-cough (VAS) (mm) (filled diamonds), throat irritation (VAS) (mm) (filled squares), and throat cooling (VAS) (mm) (filled upward triangles) and on the right, median cough frequency (coughs/hour) for baseline (open circles) and treatment (filled circles), versus time after treatment (hours).

When the data for throat irritation, urge-to-cough, and throat cooling are overlaid with the data for cough frequency (baseline and treatment) (see FIG. 11), the temporal relationships between sensations and possible antitussive effect may be assessed. The data suggest that the throat cooling sensation preceded (and had resolved before) the subsequent improvements in throat irritation and urge-to-cough. This suggests that the main mechanism of action is not one of counter-irritation. This also suggests that the observed effects (e.g., reduced coughing frequency) are not solely due to a placebo effect, because the patients will have experienced the immediate effects (i.e., throat cooling) subsiding. The data also suggest that improvements in throat irritation and urge-to-cough may be precursors for improvements in cough frequency.

Results—Global Rating of Change Scales (GRCS)

The Global Rating of Change Scale (GRCS) assessment data obtained 4 hours after treatment and 24 hours after treatment are summarized in the following table.

TABLE 11

Global Rating of Change Scale (GRCS)

|  |  | 4 hours after treatment | 24 hours after treatment |
|---|---|---|---|
| Cough Frequency | n | 12 | 11* |
|  | better | 4 (33.3%) | 4 (36.4%) |
|  | about the same | 7 (58.3%) | 6 (54.5%) |
|  | worse | 1 (8.3%) | 1 (9.1%) |
| Cough Severity | n | 12 | 11* |
|  | better | 5 (41.7%) | 4 (36.4%) |
|  | about the same | 6 (50%) | 6 (54.5%) |
|  | worse | 1 (8.3%) | 1 (9.1%) |

*One patient provided GRCS at 4 hours but not 24 hours.

Efficacy Conclusions

Based on the data, the following conclusions may be reached:

AX-8 significantly reduced cough frequency during waking hours in refractory chronic cough (RCC) patients compared with baseline (no therapy) in this uncontrolled pilot study.

The effect appears to be most marked over 4-8 hours.

The effect was accompanied by reduction in patient-reported cough severity.

The effect was also accompanied by reduction in patient-reported throat irritation and urge-to-cough, both of which are sensations associated with coughing in patients with refractory chronic cough.

Throat cooling was experienced only transiently and appeared to precede improvements in cough frequency, cough severity, and sensations associated with cough.

Additional Studies: Mode-of-Action

The mode-of-action by which the compound, [((1R,2S,5R)-2-isopropyl-5-methyl-cyclohexanecarbonyl)-amino]-acetic acid isopropyl ester (also referred to herein as "AX-8"

or "Gly-O-iPr"), acts in the treatment of chronic cough (CC) (including, for example, refractory chronic cough (RCC) and idiopathic chronic cough (ICC)) is not yet completely understood, in part because the mechanism of CC (including, e.g., RCC, ICC) is still poorly understood.

The compound is an agonist of the transient receptor potential melastatin 8 (TRPM8) cation ion channel, also referred to as cold and menthol receptor 1 (CMR1).

However, evidence suggests that the unique combination of several properties of the compound (e.g., topical mode of action; high potency; high selectivity over TRPM8; high efficacy on specific target tissues, e.g., on non-keratinized stratified epithelia—NKSE), as compared to other TRPM8 agonists and known antitussive drugs, gives rises to its unexpected efficacy for treatment of CC (including, e.g., RCC, ICC).

Menthol is the archetypal agonist of the TRPM8 ion channel. Menthol has been used in antitussive over-the-counter (OTC) treatments for decades. The efficacy of menthol is recognized in acute cough, even though several studies could not demonstrate a significant antitussive effect (see, e.g., Kenia et al., 2008; Haidl et al., 2001). Menthol has never been shown to improve chronic coughing in CC patients; instead, it has been shown to improve evoked cough (see, e.g., Millqvist et al., 2013). Moreover, menthol can induce adverse reactions such as airway irritation, dyspnea, increased mucus production with simultaneously reduced ciliary activity leading to mucus stagnation, chest tightness, and potentially respiratory failure, mainly in children, when inhaled; and acid reflux and heartburn when taken orally (see, e.g., Gavliakova et al., 2013).

Menthol's antitussive effect (see, e.g., Maher et al., 2014) and some of its side effects may be due to its activity on targets other than TRPM8. Dozens of publications have demonstrated that menthol can significantly influence the functional characteristics of a number of different kinds of channels and receptors, including TRP channels (TRPA1, TRPV1, TRPV3; see, e.g., Takaishi et al., 2016), other ligand-gated channels (e.g., GABAa, Glycine, nACh, and 5-HT3 receptors), G-protein coupled receptors (e.g., kappa-opioid receptors; see, e.g., Galeotti et al., 2002) and voltage-gated channels (e.g., voltage-gated sodium and calcium channels) (for review see Oz et al., 2017). Camphor and eucalyptol, each of which is also an agonist of the TRPM8 ion channel, are also used in cold and cough over-the-counter (OTC) treatments. Like menthol, they are poorly selective and suffer from potential adverse effects (see, e.g., Gavliakova et al., 2013).

AX-8 potency was assessed using Fluorescence Imaging Plate Reader (FLIPR®) assays (study performed by ChanTest/Charles River). The in vitro effects were evaluated on cloned human TRPM8 channels expressed in CHO cells using a Fluo-8 calcium kit and a Fluorescence Imaging Plate Reader (FLIPRTETRA™) instrument. Changes is fluorescence intensity, reflecting the calcium flux through hTRPM8, were measured and the area under the signals (area under the curve, AUC) calculated and expressed in relative light units. Changes induced by the vehicle (HEPES-buffered physiological saline solution, HB-PS) were subtracted. The half-maximal response concentrations ($EC_{50}$) were calculated, demonstrating that AX-8 is almost 6 times more potent than menthol, as a TRPM8 agonist (respectively, $EC_{50}$=0.39 µM and 2.29 µM, n=8; see FIG. 12 and FIG. 13).

Figure 12:
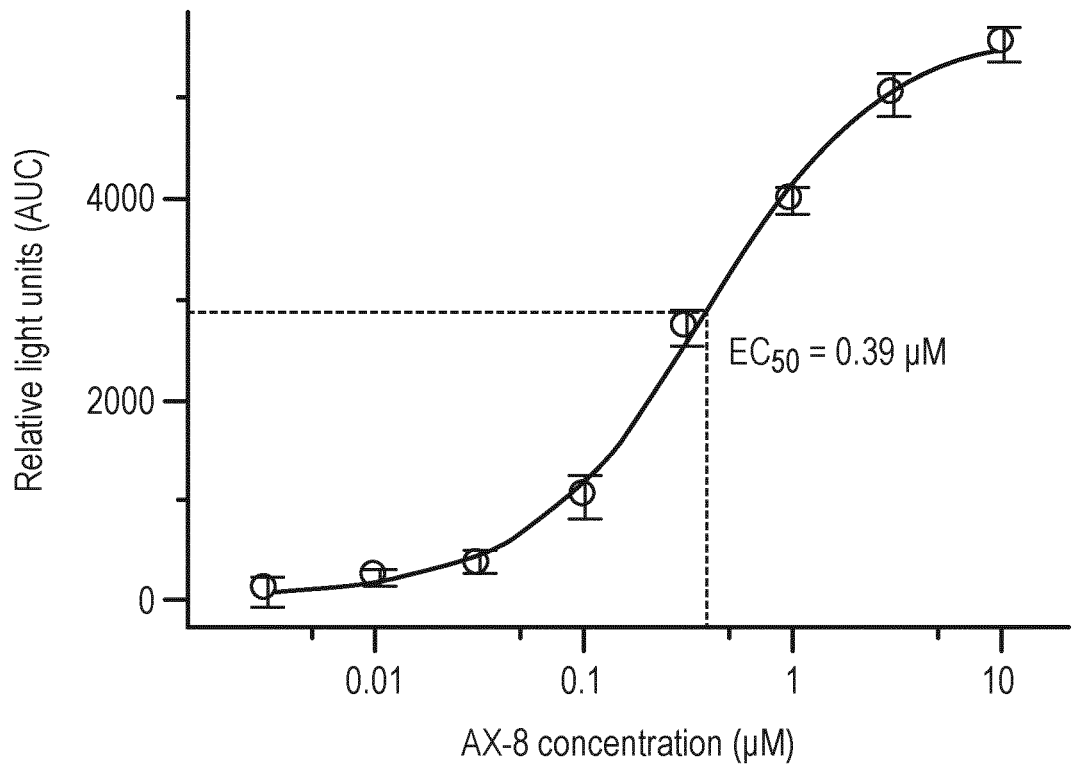
FIG. 12 is a graph representing the activation of human TRPM8 by AX-8, as obtained by FLIPR® assay. The dose response curve is represented as the calcium signal expressed in relative light units (calculated by the area under the curve—AUC, mean±sem, n=8) by the AX-8 concentration (μM, log scale). The half-maximal response concentration ($EC_{50}$) for AX-8 was found to be 0.39 μM.

Similarly, selectivity against hTRPA1 (expressed in CHO) and hTRPV1 (expressed in HEK-293) was assessed using FLIPR® calcium assay (at 100 µM, i.e., 10-fold more than the concentration for maximal response; see FIG. 12). Indeed, menthol has been shown to have a bimodal activity on TRPA1 (see, e.g., Karashima et al., 2007) and to inhibit TRPV1 (see, e.g., Takaishi et al., 2016), two thermo-sensitive ion channels related to TRPM8 and expressed in nociceptors (sensory neurons responding to harmful stimuli). For the agonist effect assessment, the effect of AX-8 was evaluated in the absence of the positive control agonist. The maximal signal elicited in the presence of the respective agonist (300 µM mustard oil for TRPA1; 3 µM capsaicin for TRPV1) was set to 100% activation and the signal in the presence of the vehicle control (HB-PS) was set to 0% activation. For the antagonist effect assessment, the channels were activated with the respective positive control agonist (100 µM mustard oil for TRPA1; 0.1 µM capsaicin for TRPV1). The effects of AX-8 to inhibit the signal was examined after agonist stimulation and compared to the respective positive control antagonist (3 µM ruthenium red). For each channel, the signal elicited in the presence of the respective positive control agonist was set to 100 (0% inhibition) and the signal in the presence of the respective positive control antagonist was set to 0 (100% inhibition). The assay demonstrated that AX-8 is selective on TRPM8 channels, with no agonistic or antagonistic interactions with TRPV1 and TRPA1 channels being observed (see FIG. 14 for the agonistic effect).

FIG. 12 is a graph representing the activation of human TRPM8 by AX-8, as obtained by FLIPR® assay. The dose response curve is represented as the calcium signal expressed in relative light units (calculated by the area under the curve—AUC, mean±sem, n=8) by the AX-8 concentration (µM, log scale). The half-maximal response concentration ($EC_{50}$) for AX-8 was found to be 0.39 µM.

Figure 13:
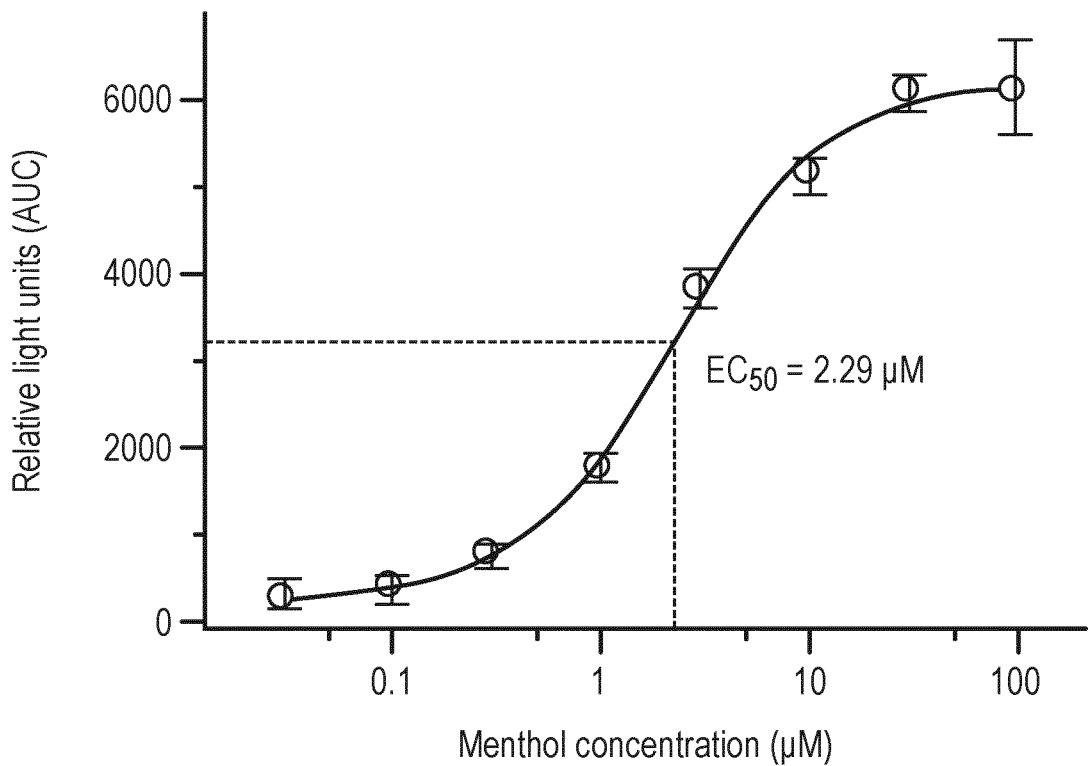
FIG. 13 is a graph representing the activation of human TRPM8 by menthol, as obtained by FLIPR® assay. The dose response curve is represented as the calcium signal expressed in relative light units (calculated by the area under the curve—AUC, mean±sem, n=8) by the menthol concentration (μM, log scale). The half-maximal response concentration ($EC_{50}$) for menthol was found to be 2.29 μM.

FIG. 13 is a graph representing the activation of human TRPM8 by menthol, as obtained by FLIPR® assay. The dose response curve is represented as the calcium signal expressed in relative light units (calculated by the area under the curve—AUC, mean±sem, n=8) by the menthol concentration (µM, log scale). The half-maximal response concentration ($EC_{50}$) for menthol was found to be 2.29 µM.

Figure 14:
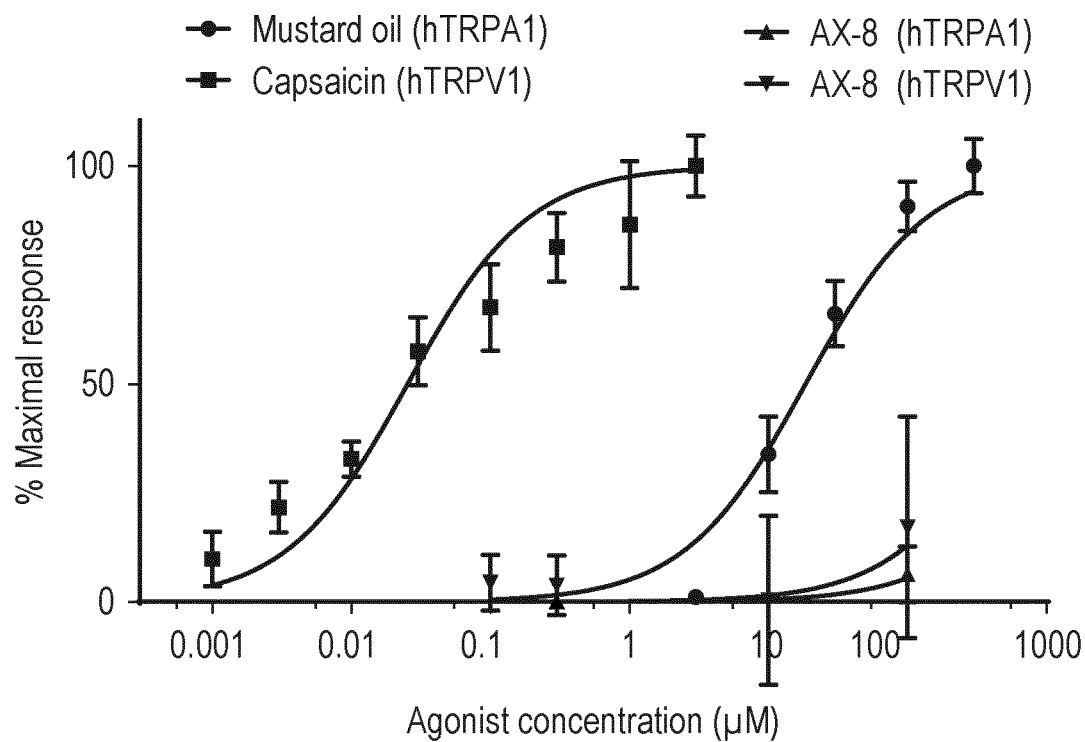
FIG. 14 is a graph representing the comparative activation of human TRPA1 and human TRPV1 by AX-8 and their reference agonists. For hTRPA1, dose response curves for mustard oil (reference TRPA1 agonist) and AX-8 are represented as the percentage of the mustard oil maximal response (mean±SD, n=4) by the agonist concentration (μM, log scale). The data demonstrate that AX-8 has no significant agonistic activity on hTRPA1 for concentrations ≤100 μM. For hTRPV1, dose response curves for capsaicin (reference TRPV1 agonist) and AX-8 are represented as the percentage of the capsaicin maximal response (mean±SD, n=4) by the agonist concentration (μM, log scale). The data demonstrate that AX-8 has no agonistic activity on hTRPV1 for concentrations ≤100 μM.

FIG. 14 is a graph representing the comparative activation of human TRPA1 and human TRPV1 by AX-8 and their reference agonists. For hTRPA1, dose response curves for mustard oil (reference TRPA1 agonist) and AX-8 are represented as the percentage of the mustard oil maximal response (mean±SD, n=4) by the agonist concentration (µM, log scale). The data demonstrate that AX-8 has no significant agonistic activity on hTRPA1 for concentrations ≤100 µM. For hTRPV1, dose response curves for capsaicin (reference TRPV1 agonist) and AX-8 are represented as the percentage of the capsaicin maximal response (mean±SD, n=4) by the agonist concentration (µM, log scale). The data demonstrate that AX-8 has no agonistic activity on hTRPV1 for concentrations ≤100 µM.

In addition, an off-target pharmacology study (Safety-Screen87 assay by Eurofins Pharma Discovery Services) has been performed. This assay package consists of 87 primary molecular targets including 13 enzyme and 74 binding assays, representing potential safety issues. No significant responses were observed with 100 µM AX-8, confirming the high selectivity of AX-8 in its effective range of concentration.

The vagal nerve is the main afferent pathway of the cough reflex loop. Therefore, the ability—and dependence on TRPM8—of AX-8 to inhibit the capsaicin-induced depolarization on isolated guinea pig vagal nerves was assessed. The tissue was assayed using an $O_2/CO_2$ gassed, grease-gap recording system as previously described (see, e.g., Birrell et al., 2009). Briefly, after the tissue has stabilised, it was exposed to a challenge (capsaicin, 1 µM, TRPV1 agonist for 2 minutes), then washed. This was then repeated to confirm the basal response. After washing, the tissue was incubated with vehicle or AX-8 (10 nM-1 mM) for 10 minutes. Following this, the tissue was re-challenged with capsaicin (in the presence of vehicle or AX-8). After a wash phase, the tissue was stimulated with capsaicin to demonstrate tissue viability and recovery of the response.

Where the TRPM8 antagonist PF-05105679 (PF, 10 µM) was used, following the two reproducible responses to capsaicin, the nerve was incubated with the TRPM8 antagonist or vehicle (0.1% DMSO) for 10 minutes, prior to incubation with AX-8 or vehicle for 10 minutes. The nerve was then restimulated with capsaicin in the presence of PF/Vehicle and AX-8/Vehicle and the percentage of inhibition of the original response calculated. Following a wash period, the nerve was then restimulated with capsaicin to determine viability. The level of depolarization was recorded at each phase. The data were recorded as actual depolarisation levels and as a percentage inhibition (caused by the vehicle or test compound) of the mean of the initial, control recordings.

Figure 15:
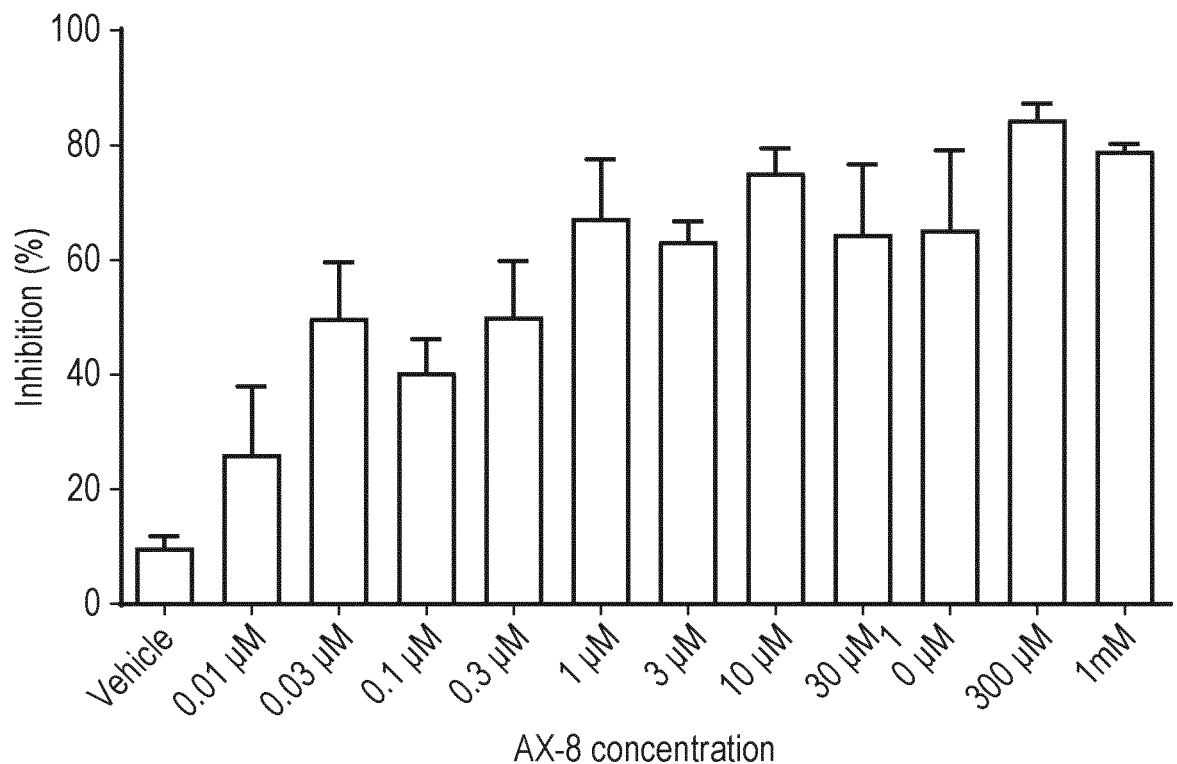
FIG. 15 is a bar graph representing the inhibition (%) of the capsaicin-induced response by AX-8 in guinea pig vagal nerve explants versus the concentration (μM) of AX-8. Capsaicin-induced response in guinea pig vagal nerves is blocked in a dose-dependent manner by AX-8 (n=3).

This study demonstrated that AX-8 inhibits up to 80% of the capsaicin-induced response in guinea pig vagal nerve explants, in a dose-dependent manner (see FIG. 15, n=3, i.e., tissue from 3 different guinea pigs). This inhibition was suppressed by pre-application of the TRPM8 antagonist PF-05105679, confirming that the effect of AX-8 is mediated by a selective activation of TRPM8 (see FIG. 16, n=4). By comparison, menthol inhibits capsaicin-induced response in guinea pig vagal nerve explants in a TRPM8-independent way (see, e.g., Maher et al., 2014).

FIG. 15 is a bar graph representing the inhibition (%) of the capsaicin-induced response by AX-8 in guinea pig vagal nerve explants versus the concentration (µM) of AX-8. Capsaicin-induced response in guinea pig vagal nerves is blocked in a dose-dependent manner by AX-8 (n=3).

Figure 16:
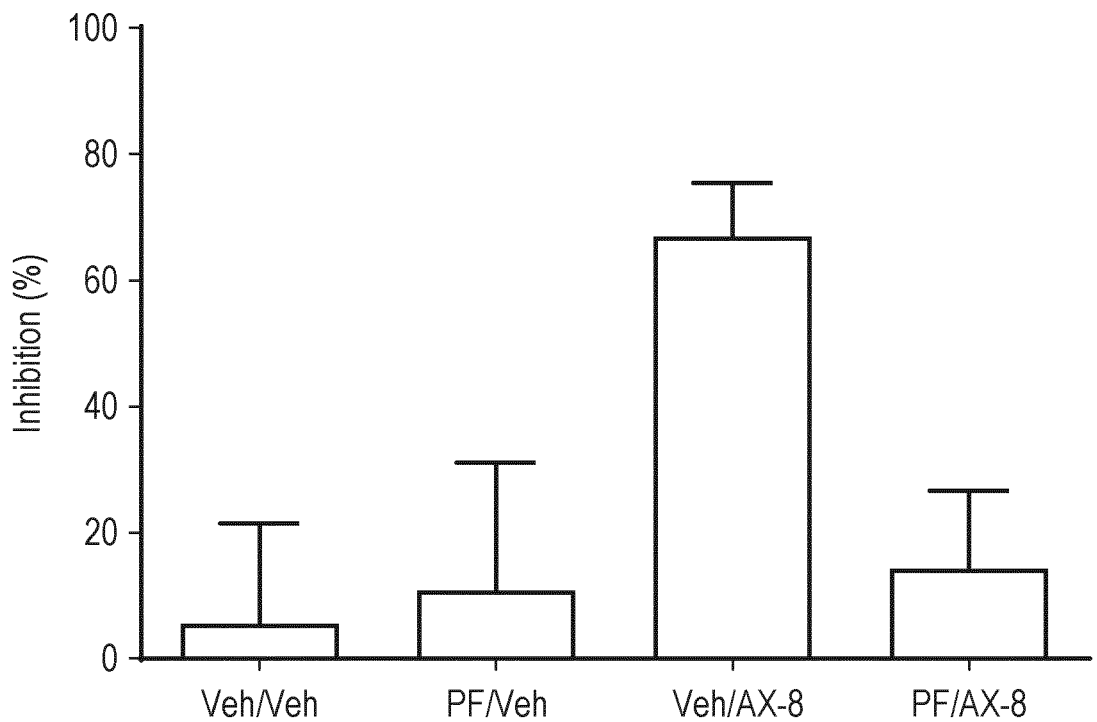
FIG. 16 is a bar graph representing the inhibition (%) of the capsaicin-induced response by AX-8 (1 μM) in guinea pig vagal nerve explants in the presence or absence of the selective TRPM8 antagonist PF-05105679 (PF, 10 μM). Four different conditions of two consecutive 10-minute incubations were done as follows: Vehicle (0.1% DMSO)/Vehicle, PF/Vehicle, Vehicle/AX-8 and PF/AX-8 (n=4). Inhibition of the response induced in guinea pig vagal nerve explants by the irritant capsaicin was blocked by the selective TRPM8 inhibitor PF-05105679, demonstrating that the effect of AX-8 is TRPM8-dependent.

FIG. 16 is a bar graph representing the inhibition (%) of the capsaicin-induced response by AX-8 (1 µM) in guinea pig vagal nerve explants in the presence or absence of the selective TRPM8 antagonist PF-05105679 (PF, 10 µM). Four different conditions of two consecutive 10-minute incubations were done as follows: Vehicle (0.1% DMSO)/Vehicle, PF/Vehicle, Vehicle/AX-8 and PF/AX-8 (n=4). Inhibition of the response induced in guinea pig vagal nerve explants by the irritant capsaicin was blocked by the selective TRPM8 inhibitor PF-05105679, demonstrating that the effect of AX-8 is TRPM8-dependent.

AX-8's antitussive effect was evaluated in a standardized guinea pig model of cough (see, e.g., Brozmanova et al., 2012; Dong et al., 2016). Guinea pigs were placed in a plethysmography chamber and exposed for 10 minutes to nebulized capsaicin solution (0.1 mM) to induce cough. The cough frequency was detected as a transient change in airflow in the chamber and the signal recorded via a pressure transducer and computer. Additionally, the audio-amplified count was also recorded electronically. Coughs were counted for the 10-minute exposure period. The experiment was visually monitored by the investigator. A 5 mg/mL AX-8 solution was prepared by dissolving AX-8 in absolute ethanol at 200 mg/mL and then diluting in a solution of 4 mg/mL of sweet potato powder in saline (i.e., vehicle).

The baseline frequency of coughing in response to exposure to capsaicin mist was recorded for the control (vehicle only) and treated (AX-8) group of animals (n=10 animals per group). Seven days later, animals were anesthetized with diethyl ether and a small animal laryngoscope was used to place the tip of a micro sprayer syringe in the oral cavity. Vehicle or AX-8 was administered into the oropharyngeal region at 75 µL per animal (n=10 animals per group). This corresponds to a dose of 0.375 mg per animal. Ten minutes after administration, the guinea pigs were exposed to the capsaicin mist and the number of coughs recorded.

Figure 17:
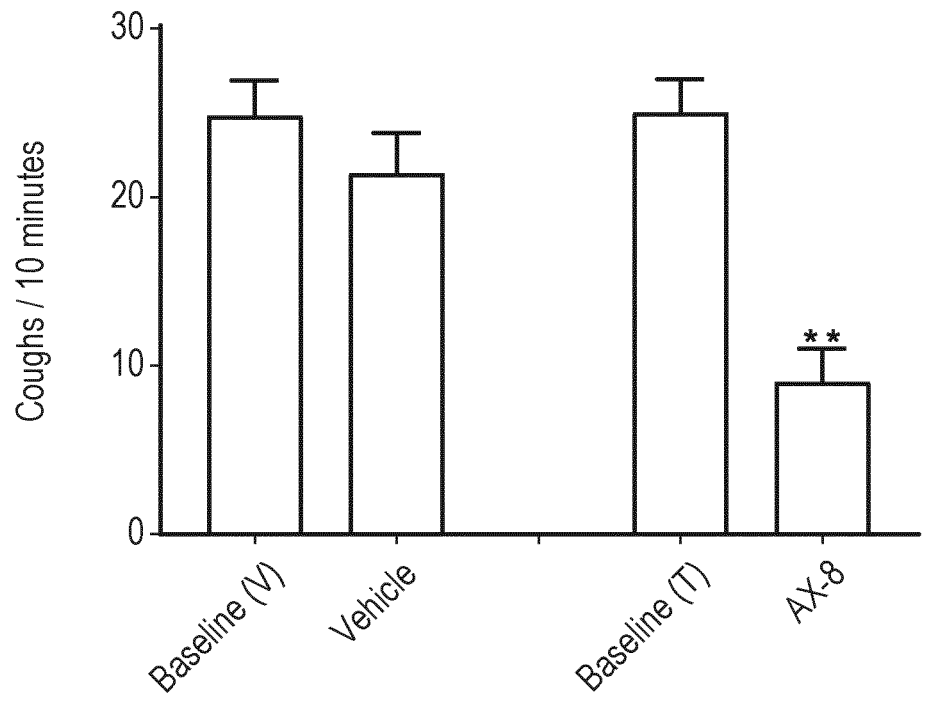
FIG. 17 is a bar graph representing the effect of AX-8 on capsaicin-induced cough in awake guinea pig. Vehicle did not significantly affect capsaicin-induced cough (Baseline (V)=24.8±2.1 coughs/10 min vs. vehicle=21.4±2.4 coughs/10 min) in guinea pigs. 75 μL of a 5 mg/mL AX-8 solution (i.e., 0.375 mg/animal) sprayed in the oropharyngeal region inhibited capsaicin-induced cough of the guinea pig from 25.0±2.0/10 min coughs (Baseline (T)) to 9.0±2.0/10 min coughs (**p<0.01). The number of animals is 10 per group (n=10).

AX-8 solution inhibited significantly capsaicin-induced cough (p<0.01, see FIG. 17).

FIG. 17 is a bar graph representing the effect of AX-8 on capsaicin-induced cough in awake guinea pig. Vehicle did not significantly affect capsaicin-induced cough (Baseline (V)=24.8±2.1 coughs/10 min vs. vehicle=21.4±2.4 coughs/10 min) in guinea pigs. 75 µL of a 5 mg/mL AX-8 solution (i.e., 0.375 mg/animal) sprayed in the oropharyngeal region inhibited capsaicin-induced cough of the guinea pig from 25.0±2.0/10 min coughs (Baseline (T)) to 9.0±2.0/10 min coughs (**p<0.01). The number of animals is 10 per group (n=10).

Similarly, the putative site of action of the investigational medical product (IMP) containing AX-8 to treat CC (including, e.g., RCC, ICC) is on the upper respiratory and digestive tracts: the surface of the oropharyngeal mucosa—at the back of the buccal cavity—and the oesophagus. Therefore, the expected mode of action of AX-8 as antitussive is through the activation of TRPM8-expressing sensory nerve endings in this region. The lining mucosa of oral cavity and oesophagus are typical examples of non-keratinized stratified squamous epithelia (NKSE). AX-8 is a potent, long acting, and selectively cooling agent for non-keratinized epithelial tissues (and permeable keratinized tissues such as eyelid skin) as compared to keratinized epithelial tissues, and as compared to other related cooling agents (e.g., Gly-OEt also known as WS-5, see, e.g., Wei et al., 2012). These unique properties not only differentiate AX-8 from other TRPM8 agonists, but most likely also act synergistically to give rise to the unexpected efficacy of AX-8 as an effective antitussive for use in the treatment of CC (including, e.g., RCC, ICC).

REFERENCES

A number of publications are cited herein in order to more fully describe and disclose the invention and the state of the art to which the invention pertains. Full citations for these publications are provided below.

Each of these publications is incorporated herein by reference in its entirety into the present disclosure, to the same extent as if each individual publication was specifically and individually indicated to be incorporated by reference.

Abdulqawi et al., 2015, "P2X3 receptor antagonist (AF-219) in refractory chronic cough: a randomised, double-blind, placebo-controlled phase 2 study", *The Lancet*, Vol. 385, pp. 1198-1205.

Baylie et al., 2010, "Inhibition of the cardiac L-type calcium channel current by the TRPM8 agonist, (-)-menthol", *J. Physiol. Pharmacol. Off. J. Pol. Physiol. Soc.*, Vol. 61, pp. 543-550.

Belvisi et al, 2017, "XEN-D0501, a Novel Transient Receptor Potential Vanilloid 1 Antagonist, Does Not Reduce Cough in Patients with Refractory Cough", *Am. J. Respir. Crit. Care Med.*, Vol. 196, pp. 1255-1263.

Birrell et al., 2009, "TRPA1 Agonists Evoke Coughing in Guinea Pig and Human Volunteers", *Am J Respir Crit Care Med.*, Vol. 180, pp 1042-1047.

Birring et al., 2003, "Development of a symptom specific health status measure for patients with chronic cough: Leicester Cough Questionnaire (LCQ)", *Thorax*, Vol. 58, pp. 339-343.

Birring, 2017, "The search for the hypersensitivity in chronic cough", *Eur. Respir. J.*, Vol. 49, Article 1700082.

Bolser, 2004, "Experimental models and mechanisms of enhanced coughing", *Pulm. Pharmacol. Ther.*, Vol. 17, pp. 383-388.

Bonvini et al., 2016, "Transient receptor potential cation channel, subfamily V, member 4 and airway sensory afferent activation: Role of adenosine triphosphate", *J Allergy Clin Immunol.*, Vol. 138(1), pp. 249-261.

Brozmanova et al., 2012, "Comparison of TRPA1-versus TRPV1-mediated cough in guinea pigs", *Eur J Pharmacol.*, Vol. 689, pp 211-218.

Canning et al., 2014, "Anatomy and neurophysiology of cough: CHEST Guideline and Expert Panel report", *Chest*, Vol. 146, pp. 1633-1648.

Chow et al., 2017, "Animal Models of Chronic Obstructive Pulmonary Disease" in *COPD—An Update in Pathogenesis and Clinical Management* (editor: McCarthy) (DOI: 10.5772/intechopen.70262).

Chung et al., 2013, "Chronic cough as a neuropathic disorder", *Lancet Respir. Med.*, Vol. 1, pp. 414-422.

Chung, 2014, "Approach to chronic cough: the neuropathic basis for cough hypersensitivity syndrome", *J. Thorac. Dis.*, Vol. 6, pp. S699-S707.

Dong et al., 2016, "A TRPM8 Agonist Ax-8 Inhibits Capsaicin-Induced Cough in Guinea Pig", *Chest*, Vol. 149, pp. A545-A545.

EudraCT Number 2013-002728-17, "A Phase 2a, Multi-Centre, Randomised, Double-Blind, Parallel Group, Placebo-Controlled Study to Evaluate Efficacy, Safety and Tolerability of Inhaled GRC 17536, Administered for 4 Weeks, in Patients with Refractory Chronic Cough", https://www.clinicaltrialsregister.eu/ctr-search/trial/2013-002728-17/GB.

Ford et al., 2006, "Cough in the community: a cross sectional survey and the relationship to gastrointestinal symptoms", *Thorax*, Vol. 61, pp. 975-979.

Galeotti et al., 2002, "Menthol: a natural analgesic compound", *Neurosci. Lett.*, Vol. 322, pp. 145-148.

Gavliakova et al., 2013, "Analysis of pathomechanisms involved in side effects of menthol treatment in respiratory diseases", *Open J. Mol. Integr. Physiol.*, Vol. 03, pp. 21-26.

Gibson et al., 2015, "Management of chronic refractory cough", *BMJ*, 2015, Vol. 351, Article h5590.

Haidl et al., 2001, "Does the inhalation of a 1% L-menthol solution in the premedication of fiberoptic bronchoscopy affect coughing and the sensation of dyspnea?", *Pneumol. Stuttg. Ger.*, Vol. 55, pp. 115-119.

Karashima et al., 2007, "Bimodal Action of Menthol on the Transient Receptor Potential Channel TRPA1", *J. Neurosci.*, Vol. 27, pp. 9874-9884.

Kenia et al., 2008, "Does inhaling menthol affect nasal patency or cough?", *Pediatr. Pulmonol.*, Vol. 43, pp. 532-537.

Khalid et al., 2014, "Transient receptor potential vanilloid 1 (TRPV1) antagonism in patients with refractory chronic cough: a double-blind randomized controlled trial", *J. Allergy Clin. Immunol.*, Vol. 134, No. 2, pp. 56-62.

Ludbrook et al., 2019, "S27 A placebo-controlled, double-blind, randomised, crossover study to assess the efficacy, safety and tolerability of TRPV4 inhibitor GSK2798745 in participants with chronic cough", *Thorax*, Vol. 74 (Suppl 2), pp. A18-A18.

Maher et al., 2014, "P6 Menthol Has Beneficial Effects In The Airways Through A Trpm8-independent Mechanism", *Thorax*, Vol. 69, pp. A79-A80.

Mazzone et al., 2018, "The heterogeneity of chronic cough: a case for endotypes of cough hypersensitivity", *Lancet Respir Med.*, Vol. 6(8), pp 636-646.

McGarvey, 2005, "Idiopathic chronic cough: a real disease or a failure of diagnosis?", *Cough Lond. Engl.*, Vol. 1, p. 9.

Melanaphy et al., 2016, "Effects of menthol on rat tail artery mediated by TRPM8 and voltage-gated calcium channels", *Am. J. Physiol. Heart Circ. Physiol.*, Vol. 311, No. 6, pp. 1416-1430.

Millqvist et al., 2013, "Inhalation of menthol reduces capsaicin cough sensitivity and influences inspiratory flows in chronic cough", *Respir. Med.*, Vol. 107, pp. 433-438.

Morice et al., 2006, "Recommendations for the management of cough in adults", *Thorax*, Vol. 61 (Suppl 1), pp. i1-i24.

Morice et al., 2011, "Hypersensitivity Syndrome: A Distinct Clinical Entity", *Lung*, Vol. 189, pp. 73-79.

Morice et al., 2017, "The Effect of MK-7264, a P2X3 antagonist, on Cough Reflex Sensitivity in a Randomized Crossover Trial of Healthy and Chronic Cough Subjects", *Eur. Respir. J.*, Vol. 50, OA2931.

Mukhopadhyay et al., 2016, "Blocking TRPA1 in Respiratory Disorders: Does It Hold a Promise?", *Pharmaceuticals (Basel)*, Vol. 9(4), Article 70.

Oz et al., 2017, "Cellular and Molecular Targets of Menthol Actions", *Front. Pharmacol.*, Vol. 8, Article 472.

Pavord et al., 2008, "Management of chronic cough", *The Lancet*, Vol. 371, pp. 1375-1384.

Polverino et al., 2012, "Anatomy and neuro-pathophysiology of the cough reflex arc", *Multidiscip. Respir. Med.*, Vol. 7, p. 5.

Ryan et al., 2018, "An update and systematic review on drug therapies for the treatment of refractory chronic cough", *Expert Opin. Pharmacother.*, Vol. 19, pp. 687-711.

Smith et al., 2020, "Gefapixant, a P2X3 receptor antagonist, for the treatment of refractory or unexplained chronic cough: a randomised, double-blind, controlled, parallel-group, phase 2b trial", *Lancet Respir. Med.*, DI: 10.1016/S2213-2600(19)30471-0.

Smith et al., 2016, "S27 The effect of P2X3 antagonism (AF-219) on experimentally evoked cough in healthy volunteers and chronic cough patients", *Thorax*, Vol. 71, pp. A17-A17.

Smith et al., 2017a, "Inhibition of P2X3 by MK-7264 reduces 24-hour cough frequency in a randomized, controlled, Phase 2b clinical trial", *Eur. Respir. J.*, Vol. 50, OA2932.

Smith et al., 2017b, "MK-7264, a P2X3 Receptor Antagonist, Reduces Cough Frequency in Patients with Refractory Chronic Cough: Results from a Randomized, Controlled, Phase 2b Clinical Trial", *Am. J. Respir. Crit. Care Med.*, Vol. 195, pp. A7608-A7608.

Smith et al., 2017c, "Effects of a novel sodium channel blocker, GSK2339345, in patients with refractory chronic cough", *Int, J. Clin. Pharmacol. Ther.*, Vol 55, pp. 712-719.

Song et al., 2017, "Cough Hypersensitivity Syndrome: A Few More Steps Forward", *Allergy Asthma Immunol. Res.*, Vol. 9, pp. 394-402.

Takaishi et al., 2016, "Reciprocal effects of capsaicin and menthol on thermosensation through regulated activities of TRPV1 and TRPM8", *J. Physiol. Sci.*, Vol. 22, No. 2, pp. 143-155.

Vogt-Eisele et al., 2007, "Monoterpenoid agonists of TRPV3", *Br. J. Pharmacol.*, Vol. 151, pp. 530-540.

Wei et al., 2012, "[((1R,2S,5R)-2-Isopropyl-5-methyl-cyclohexanecarbonyl-amino]-acetic acid isopropyl ester and related compounds and their use in therapy", United States patent publication number US 2012/0251461 A1, published 4 Oct. 2012.

Wei et al., 2012, "[((1R,2S,5R)-2-Isopropyl-5-methyl-cyclohexanecarbonyl-amino]-acetic acid isopropyl ester and related compounds and their use in therapy", international patent (PCT) publication number WO 2012/076831 A1, published 14 Jun. 2012.

Xu et al., 2016, "Establishment of chronic cough model in guinea pigs by citric acid inhalation", *Chest*, Vol. 149, pp. A543-A543.

The invention claimed is:

1. A method of treatment of refractory chronic cough (RCC) or idiopathic chronic cough (ICC) comprising administering to a patient in need thereof a therapeutically effective amount of a compound that is [((1R,2S,5R)-2-isopropyl-5-methyl-cyclohexanecarbonyl)-amino]-acetic acid isopropyl ester, or a pharmaceutically acceptable salt, hydrate, or solvate thereof.

2. The method according to claim 1, wherein the treatment is treatment of idiopathic chronic cough (ICC).

3. The method according to claim 1, wherein the treatment is treatment of refractory chronic cough (RCC).

4. The method according to claim 1, wherein the treatment is treatment of refractory chronic cough (RCC) that persists after assessment and treatment of a cough-related condition.

5. The method according to claim 1, wherein the treatment is treatment of refractory chronic cough (RCC) that persists after assessment and treatment of: asthma, eosinophilic bronchitis, post-nasal drip syndrome (PNDS), gastro-oesophageal reflux disease (GORD), bronchiectasis chronic obstructive pulmonary disease (COPD), or idiopathic pulmonary fibrosis (IPF).

6. The method according to claim 1, wherein refractory chronic cough (RCC) or idiopathic chronic cough (ICC) is associated with allotussia.

7. The method according to claim 1, wherein refractory chronic cough (RCC) or idiopathic chronic cough (ICC) is associated with hypertussia.

8. The method according to claim 1, wherein refractory chronic cough (RCC) or idiopathic chronic cough (ICC) is associated with cough hypersensitivity syndrome (CHS).

9. The method according to claim 1, wherein refractory chronic cough (RCC) or idiopathic chronic cough (ICC) is associated with cough hypersensitivity reflex (CHR).

10. The method according to claim 1, wherein refractory chronic cough (RCC) or idiopathic chronic cough (ICC) is associated with laryngeal paraesthesia.

11. The method according to claim 1, wherein refractory chronic cough (RCC) or idiopathic chronic cough (ICC) is associated with laryngeal hypersensitivity syndrome (LHS).

12. The method according to claim 1, wherein refractory chronic cough (RCC) or idiopathic chronic cough (ICC) is sensory neuropathic cough.

13. The method according to claim 1, wherein refractory chronic cough (RCC) or idiopathic chronic cough (ICC) is associated with peripheral sensitization; central sensitization (cough centre); and/or cortical and/or subcortical maladaptive plasticity.

14. The method according to claim 1, wherein refractory chronic cough (RCC) or idiopathic chronic cough (ICC) is associated with vagal neuropathy.

15. The method according to claim 1, wherein refractory chronic cough (RCC) or idiopathic chronic cough (ICC) is associated with airway inflammation.

16. The method according to claim 1, wherein refractory chronic cough (RCC) or idiopathic chronic cough (ICC) is associated with neurogenic inflammation and/or neuroinflammation.

17. The method according to claim 1, wherein:
the treatment is to reduce cough frequency;
the treatment is to reduce hourly cough frequency;
the treatment is to reduce median hourly cough frequency;
the treatment is to reduce mean hourly cough frequency;
the treatment is to reduce awake hourly cough frequency;
the treatment is to reduce awake median hourly cough frequency;
the treatment is to reduce awake mean hourly cough frequency;
the treatment is to reduce asleep hourly cough frequency;
the treatment is to reduce asleep median hourly cough frequency;
the treatment is to reduce asleep mean hourly cough frequency;
the treatment is to reduce cough severity;
the treatment is to reduce urge-to-cough; and/or
the treatment is to reduce throat irritation.

18. The method according to claim 1, wherein:
the treatment is by topical oral administration of the compound;
the treatment is by topical oromucosal administration of the compound;
the treatment is by topical buccal administration of the compound;
the treatment is by topical sublingual administration of the compound;
the treatment is by topical intranasal administration of the compound; or
the treatment is by topical transmucosal administration of the compound.

19. The method according to claim 1, comprising administering to the patient from about 1 µg to about 5 mg of the compound per kilogram body weight of the patient per day.

20. The method according to claim 1, comprising administering to the patient from about 0.07 mg to about 350 mg of the compound per day.

21. The method according to claim 1, wherein:
the treatment is by a treatment regimen of 1 to 5 administrations daily.

22. The method according to claim 1, wherein the treatment is by a pro re nata (PRN) treatment regimen.

23. The method according to claim 1, wherein:
the compound is formulated as a tablet;
the compound is formulated as an orally disintegrating tablet (ODT);
the compound is formulated as a lozenge;
the compound is formulated as a spray;
the compound is formulated as a mist; or
the compound is formulated as an aerosol.

24. The method according to claim 1, wherein the compound is [((1R,2S,5R)-2-isopropyl-5-methyl-cyclohexanecarbonyl)-amino]-acetic acid isopropyl ester.

25. The method according to claim 1, comprising administering to the patient 2 mg to 30 mg of [((1R,2S,5R)-2-isopropyl-5-methyl-cyclohexanecarbonyl)-amino]-acetic acid isopropyl ester.

26. The method according to claim 1, comprising administering to the patient an orally disintegrating tablet (ODT) comprising 2 mg to 30 mg of [((1R,2S,5R)-2-isopropyl-5-methyl-cyclohexanecarbonyl)-amino]-acetic acid isopropyl ester.

27. The method according to claim 1, comprising administering to the patient an orally disintegrating tablet (ODT) comprising 5 mg of [((1R,2S,5R)-2-isopropyl-5-methyl-cyclohexanecarbonyl)-amino]-acetic acid isopropyl ester.

28. The method according to claim 1, comprising administering to the patient [((1R,2S,5R)-2-isopropyl-5-methyl-cyclohexanecarbonyl)-amino]-acetic acid isopropyl ester three times daily.

29. The method according to claim 1, comprising administering to the patient an orally disintegrating tablet (ODT) comprising [((1R,2S,5R)-2-isopropyl-5-methyl-cyclohexanecarbonyl)-amino]-acetic acid isopropyl ester three times daily.

30. The method according to claim 28, wherein the orally disintegrating tablet (ODT) comprises 2 mg to 30 mg of [((1R,2S,5R)-2-isopropyl-5-methyl-cyclohexanecarbonyl)-amino]-acetic acid isopropyl ester.

31. The method according to claim 28, wherein the orally disintegrating tablet (ODT) comprises 5 mg of [((1R,2S,5R)-2-isopropyl-5-methyl-cyclohexanecarbonyl)-amino]-acetic acid isopropyl ester.

32. The method according to claim 2, wherein the compound is [((1R,2S,5R)-2-isopropyl-5-methyl-cyclohexanecarbonyl)-amino]-acetic acid isopropyl ester.

33. The method according to claim 2, comprising administering to the patient 2 mg to 30 mg of [((1R,2S,5R)-2-isopropyl-5-methyl-cyclohexanecarbonyl)-amino]-acetic acid isopropyl ester.

34. The method according to claim 2, comprising administering to the patient an orally disintegrating tablet (ODT) comprising 2 mg to 30 mg of [((1R,2S,5R)-2-isopropyl-5-methyl-cyclohexanecarbonyl)-amino]-acetic acid isopropyl ester.

35. The method according to claim 2, comprising administering to the patient an orally disintegrating tablet (ODT) comprising 5 mg of [((1R,2S,5R)-2-isopropyl-5-methyl-cyclohexanecarbonyl)-amino]-acetic acid isopropyl ester.

36. The method according to claim 2, comprising administering to the patient [((1R,2S,5R)-2-isopropyl-5-methyl-cyclohexanecarbonyl) -amino]-acetic acid isopropyl ester three times daily.

37. The method according to claim 2, comprising administering to the patient an orally disintegrating tablet (ODT) comprising [((1R,2S,5R) -2-isopropyl-5-methyl-cyclohexanecarbonyl)-amino]-acetic acid isopropyl ester three times daily.

38. The method according to claim 37, wherein the orally disintegrating tablet (ODT) comprises 2 mg to 30 mg of [((1R,2S,5R)-2-isopropyl-5-methyl-cyclohexanecarbonyl)-amino]-acetic acid isopropyl ester.

39. The method according to claim 37, wherein the orally disintegrating tablet (ODT) comprises 5 mg of [((1R,2S,5R)-2-isopropyl-5-methyl -cyclohexanecarbonyl)-amino]-acetic acid isopropyl ester.

40. The method according to claim 3, wherein the compound is [((1R,2S,5R)-2-isopropyl-5-methyl-cyclohexanecarbonyl)-amino]-acetic acid isopropyl ester.

41. The method according to claim 3, comprising administering to the patient 2 mg to 30 mg of [((1R,2S,5R)-2-isopropyl-5-methyl-cyclohexanecarbonyl)-amino]-acetic acid isopropyl ester.

42. The method according to claim 3, comprising administering to the patient an orally disintegrating tablet (ODT) comprising 2 mg to 30 mg of [((1R,2S,5R)-2-isopropyl-5-methyl-cyclohexanecarbonyl)-amino]-acetic acid isopropyl ester.

43. The method according to claim 3, comprising administering to the patient an orally disintegrating tablet (ODT) comprising 5 mg of [((1R,2S,5R)-2-isopropyl-5-methyl-cyclohexanecarbonyl)-amino]-acetic acid isopropyl ester.

44. The method according to claim 3, comprising administering to the patient [((1R,2S,5R)-2-isopropyl-5-methyl -cyclohexanecarbonyl)-amino]-acetic acid isopropyl ester three times daily.

45. The method according to claim 3, comprising administering to the patient an orally disintegrating tablet (ODT) comprising [((1R,2S,5R)-2-isopropyl-5-methyl-cyclohexanecarbonyl)-amino]-acetic acid isopropyl ester three times daily.

46. The method according to claim 45, wherein the orally disintegrating tablet (ODT) comprises 2 mg to 30 mg of [((1R,2S,5R)-2-isopropyl-5-methyl-cyclohexanecarbonyl)-amino]-acetic acid isopropyl ester.

47. The method according to claim 45, wherein the orally disintegrating tablet (ODT) comprises 5 mg of [((1R,2S,5R)-2-isopropyl-5-methyl-cyclohexanecarbonyl)-amino]-acetic acid isopropyl ester.

* * * * *